United States Patent [19]

Christensen et al.

[11] Patent Number: 4,680,292

[45] Date of Patent: Jul. 14, 1987

[54] CARBAPENEMS AND 1-METHYLCARBAPENEMS HAVING A 2-HETEROARYLIUMALIPHATIC SUBSTITUENT

[75] Inventors: Burton G. Christensen, Cliffside; Thomas N. Salzmann, North Plainfield; James V. Heck, Fanwood, all of N.J.

[73] Assignee: Merck & Co., Inc., Rahway, N.J.

[21] Appl. No.: 681,180

[22] Filed: Dec. 13, 1984

[51] Int. Cl.⁴ .................. C07D 487/04; A61K 31/40
[52] U.S. Cl. .................................. 514/210; 540/350; 540/310
[58] Field of Search .............. 260/249.2 T, 249.7 R; 514/210; 540/310, 350

[56] References Cited

U.S. PATENT DOCUMENTS

| | | | |
|---|---|---|---|
| 4,189,493 | 2/1980 | Christensen et al. | 424/273 R |
| 4,218,459 | 8/1980 | Cama et al. | 424/270 |
| 4,260,627 | 4/1981 | Christensen et al. | 424/274 |
| 4,262,009 | 4/1981 | Christensen et al. | 424/274 |
| 4,262,011 | 4/1981 | Christensen et al. | 424/274 |
| 4,312,871 | 1/1982 | Christensen et al. | 424/263 |
| 4,341,706 | 7/1982 | Christensen et al. | 260/245.2 T |
| 4,347,355 | 8/1982 | Chu | 542/420 |
| 4,348,320 | 9/1982 | Bouffard et al. | 260/239 |
| 4,377,591 | 3/1983 | Hiraoka et al. | 424/274 |
| 4,465,632 | 8/1984 | Christensen et al. | 260/245.2 T |
| 4,536,335 | 8/1985 | Kim et al. | 260/245.2 R |

FOREIGN PATENT DOCUMENTS

| | | |
|---|---|---|
| 56-60852 | 10/1982 | Japan . |
| 56199682 | 6/1983 | Japan . |
| 57145086 | 2/1984 | Japan . |
| 57145087 | 2/1984 | Japan . |
| 2092147A | 8/1982 | United Kingdom . |
| 2119371A | 11/1983 | United Kingdom . |
| 2122196A | 1/1984 | United Kingdom . |
| 2128187A | 4/1984 | United Kingdom . |

Primary Examiner—Nicholas S. Rizzo
Attorney, Agent, or Firm—Hesna J. Pfeiffer; Raymond M. Speer

[57] ABSTRACT

Carbapenems and 1-methylcarbapenems having the formula:

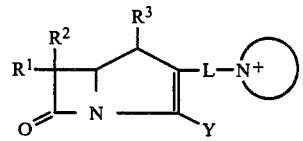

wherein
$R_1$ and $R_2$ are independently H, $CH_3$, $CH_3CH_2$—, $(CH_3)_2CH$—, $HOCH_2$, $CH_3CH(OH)$—, $(CH_3)_2C(OH)$—, $FCH_2$—, $F_2CH$, $F_3C$—, $CH_3CH(F)$—, $CH_3CF_2$—, or $(CH_3)_2C(F)$—;

$R^3$ is H— or $CH_3$;

L is
a bridging group comprising substituted or unsubstituted $C_1$-$C_4$ straight, $C_2$-$C_6$ branched or $C_3$-$C_7$ cycloalkyl groups wherein the substituents are selected from $C_1$-$C_6$ alkyl, O—$C_1$-$C_6$ alkyl, S—C-$_1$-$C_6$ alkyl, $CF_3$, $N(C_1$-$C_6$ alkyl$)_2$;

$N^+$ is a quaternary, monocyclic or bicyclic substituted or unsubstituted, heteroaryl group containing (a) when monocyclic, up to 3 heteroatoms and up to 6 total ring atoms, or (b) when bicyclic, up to 5 heteroatoms and 9-10 ring atoms, which is optionally substituted with one or more groups;

their preparation and antibiotic use are disclosed.

26 Claims, No Drawings

CARBAPENEMS AND 1-METHYLCARBAPENEMS HAVING A 2-HETEROARYLIUMALIPHATIC SUBSTITUENT

BACKGROUND OF THE INVENTION

The present invention is concerned with carbapenem and 1-methylcarbapenem antibiotics having a quaternary mono- or bicyclic heteroarylium alkyl group which is internally alkylated in the 2-position.

Thienamycin is a known carbapenem, broad spectrum antibiotic of the formula:

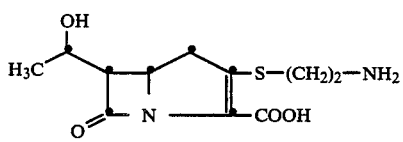

Other derivatives of A are also known.

The present internally alkylated mono- or bicyclic 2-quaternary heteroarylalkyl substituted carbapenems are believed to have an antibiotic spectrum comparable to A.

BRIEF DESCRIPTION OF DISCLOSURES IN THE ART

Sankyo U.S. Pat. No. 4,377,591 and Japanese patent publications 56-199682 and 56-60852 Shionogi Japanese patent publications 57-145086 and 57-145087; and Roche U.K. patent publication 2 092 147A, all describe azabicycloheptene antibiotics having a 2-position substituent joined through a thioalkylene bridge. U.S. Pat. No. 4,189,493 to Bristol-Myers discloses externally alkylated heteroarylium alkylthioazabicycloheptene antibiotics. U.S. Pat. No. 4,465,672, U.S. Pat. No. 4,260,627 and U.S. Pat. No. 4,267,188, all assigned to Merck & Co., Inc., disclose 2,6-substituted-1-carba-2-penem-3-carboxylic acids wherein the 2-substituent can be substituted or unsubstituted alkyl or aryl. However, none of the above 2 references specifically describe the carbapenem compounds of the present invention.

SUMMARY OF THE INVENTION

Compounds of the formula:

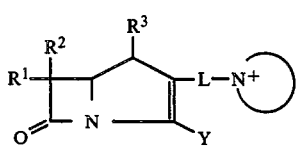

where:

$R_1$ and $R_2$ are independently H, $CH_3$, $CH_3CH_2-$, $(CH_3)_2CH-$, $HOCH_2$, $CH_3CH(OH)-$, $(CH_3)_2C(OH)-$, $FCH_2-$, $F_2CH$, $F_3C-$, $CH_3CH(F)-$, $CH_3CF_2-$, or $(CH_3)_2C(F)-$;

$R^3$ is H or $CH_3$;

L is a bridging group comprising substituted or unsubstituted $C_1$-$C_4$ straight, $C_2$-$C_6$ branched or $C_3$-$C_7$ cycloalkyl groups wherein the substituents are selected from $C_1$-$C_6$ alkyl, $O$—$C_1$-$C_6$ alkyl, $S$—$C_1$-$C_6$ alkyl, $CF_3$, $N(C_1$-$C_6$ alkyl$)_2$;

is a quaternized, monocyclic or bicyclic heteroaryl group; and Y is a carboxy containing group.

DETAILED DESCRIPTION OF THE INVENTION

The invention is embodied in a compound having the formula:

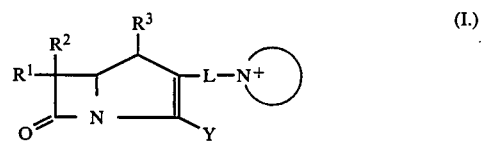

wherein:

$R^3$ is hydrogen, or methyl;

$R_1$ and $R_2$ are independently H, $CH_3$, $CH_3CH_2-$, $(CH_3)_2CH-$, $HOCH_2$, $CH_3CH(OH)-$, $(CH_3)_2C(OH)-$, $FCH_2-$, $F_2CH$, $F_3C-$, $CH_3CH(F)-$, $CH_3CF_2-$, or $(CH_3)_2C(F)-$;

L is a bridging group comprising substituted or unsubstituted $C_1$-$C_6$ straight or $C_2$-$C_6$ branched or $C_3$-$C_7$ cycloalkyl groups wherein the substituents are selected from $C_1$-$C_6$ alkyl, $O$—$C_1$-$C_6$ alkyl, $S$—$C_1$-$C_6$ alkyl, $CF_3$, $N(C_1$-$C_6$ alkyl$)_2$;

wherein

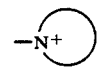

is a quaternary, monocyclic or bicyclic, substituted or unsubstituted heteroaryl group containing (a) when monocyclic, up to 3 heteroatoms and up to 6 total ring atoms or (b) when bicyclic up to 5 heteroatoms and 9-10 ring atoms, which is optionally substituted by one or more of the groups independently selected from (1) a substituted or unsubstituted $C_1$-$C_6$ alkyl, $C_2$-$C_6$ alkenyl, $C_5$-$C_7$ cycloalkenyl, $C_3$-$C_7$ cycloalkyl, or ($C_3$-$C_7$ cycloalkyl)methyl;

(2) a substituted or unsubstituted $C_3$-$C_7$ heterocycloalkyl or ($C_3$-$C_7$ heterocycloalkyl)methyl having up to 3 hetero ring atoms;

(3) an unsubstituted or substituted phenyl or heteroaryl radical;

(4) an unsubstituted or substituted phenyl($C_1$-$C_4$ alkyl) or heteroaryl($C_1$-$C_4$ alkyl) radical;

(5) a trifluoromethyl or pentafluoroethyl group;

(6) a halogen atom;

(7) an unsubstituted or substituted $C_1$-$C_4$ alkoxy radical;

(8) a hydroxyl group;

(9) an unsubstituted or substituted ($C_1$-$C_6$ alkyl)carbonyloxy radical;

(10) a carbamoyloxy radical which is unsubstituted, monosubstituted or disubstituted on the nitrogen with a $C_1$-$C_4$ alkyl group;

(11) a $C_1$-$C_6$ alkylthio radical, $C_1$-$C_6$ alkylsulfinyl radical or a $C_1$-$C_6$ alkylsulfonyl radical each of which is unsubstituted or substituted in the alkyl group;
(12) a sulfo group;
(13) a sulfamoyl group which is unsubstituted, monosubstituted, or disubstituted on nitrogen with a $C_1$-$C_4$ alkyl group,
(14) an amino group;
(15) a mono($C_1$-$C_4$ alkyl)amino or di($C_1$-$C_4$ alkyl)amino radical each of which is unsubstituted or substituted in the alkyl group;
(16) a formylamino group;
(17) an unsubstituted or substituted ($C_1$-$C_6$ alkyl)carbonylamino radical;
(18) a ($C_1$-$C_4$ alkoxy)carbonylamino radical;
(19) a ureido group in which the terminal nitrogen atom is unsubstituted or monosubstituted with a $C_1$-$C_6$ alkyl group;
(20) an arylsulfonamido or ($C_1$-$C_6$ alkyl)sulfonamido group;
(21) a cyano group;
(22) a formyl or acetalized formyl radical;
(23) an unsubstituted or substituted ($C_1$-$C_6$ alkyl)carbonyl radical wherein the carbonyl group is free or acetalized;
(24) an unsubstituted or substituted phenylcarbonyl or heteroarylcarbonyl radical;
(25) a hydroxyiminomethyl radical in which the oxygen or carbon atom is optionally substituted by a $C_1$-$C_4$ alkyl group;
(26) a carboxyl group;
(26a) a 5-tetrazolyl group;
(27) a ($C_1$-$C_6$ alkoxy)carbonyl radical;
(28) a carbamoyl radical which is unsubstituted, monosubstituted, or disubstituted on the nitrogen atom with a $C_1$-$C_4$ alkyl group;
(29) a N-hydroxy carbamoyl or N-($C_1$-$C_4$ alkoxy)carbamoyl radical in which the nitrogen atom may be additionally substituted by a $C_1$-$C_4$ alkyl group;
(30) a thiocarbamoyl group;
(31) an amidino group

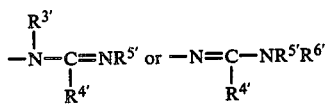

wherein $R^{3'}$, $R^{4'}$, $R^{5'}$, $R^{6'}$ are hydrogen, $C_1$-$C_4$ alkyl, or wherein two of the groups together form a $C_3$-$C_6$ alkylidine radical optionally interupted by a heteroatom and joined to either one or two nitrogen atoms to form a ring;
(32) a guanidino group in which $R^{4'}$ above is $NR^{5'}R^{6'}$;
(33) a carbamimidoyl group

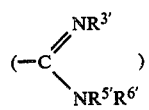

wherein $R^{3'}$, $R^{5'}$ and $R^{6'}$ are as defined above;
(34) a cyano($C_1$-$C_4$ alkyl) radical;
(35) a carboxy($C_1$-$C_4$ alkyl) radical;
(36) a sulfo($C_1$-$C_4$ alkyl) radical;
(37) a carbamoyl($C_1$-$C_4$ alkyl) radical;
(38) a hydroxy($C_1$-$C_4$ alkyl) radical;
(39) an amino($C_1$-$C_6$ alkyl) radical which is unsubstituted, monosubstituted, or disubstituted on the nitrogen atom with $C_1$-$C_4$ alkyl groups, and
(40) a 5-tetrazoyl($C_1$-$C_4$ alkyl) radical;
wherein the substituents in groups (7), (9), (11), (15), (17), (23), and (24) are selected from hydroxy, $C_1$-$C_4$alkoxy, mercapto, amino, mono- or di($C_1$-$C_4$alkyl)amino, cyano, halo, $CF_3$, COOH, sulfo, carbamoyl, and sulfamoyl, and wherein the substituents in grous (1)–(4) are selected from those defined in groups (5)–(33).

L is a bridging group comprising substituted or unsubstituted $C_1$-$C_4$ straight, $C_3$-$C_6$ branched or $C_3$-$C_7$ cycloalkyl groups wherein the substituents are selected from $C_1$-$C_6$ alkyl, O—$C_1$-$C_6$ alkyl, S—$C_1$-$C_6$ alkyl, $CF_3$, N($C_1$-$C_6$ alkyl)$_2$;

Y is
(i) —COOH, a pharmaceutically acceptable ester or salt thereof;
(ii) COOR wherein R is a removeable carboxy protecting group, e.g., p-nitrobenzyl, o-nitrobenzyl, benzyl, or allyl;
(iii) COOM wherein M is an alkali metal; or
(iv) COO$^-$ provided that when Y is other than (iv) a counterion $Z^-$ is present.

As used herein, the term "heteroatom" means nitrogen, oxygen, or sulfur, independently selected where more than one heteroatom is involved.

A preferred group of compounds of Formula I are those where L is $C_1$-$C_6$ branched or linear alkyl, both substituted and unsubstituted. The preferred substituents are OH, $CF_3$, $OC_{1-4}$alkyl, CN, $CONH_2$, CONH(-$C_1$-$C_4$alkyl), CON($C_1$-$C_4$alkyl)$_2$, COOH, $NH_2$, NH($C_1$-$C_4$alkyl), and N($C_1$-$C_4$alkyl)$_2$ and especially $OCH_3$, OH, $NH_2$, and $CF_3$. Examples of preferred L groups are —$CH_2$—, —CH($CH_3$)—, —CH($CH_2CH_3$)—, —CH($CH_2OCH_3$), —$CH_2$—$CH_2$—, —CH($CH_3$)—$CH_2$—, —CH($CH_2CH_3$)—$CH_2$—, —C($CH_3$)$_2$—$CH_2$—, —($CH_2$)$_3$—, —CH($CH_3$)—($CH_2$)$_2$—, $CH_2$—CH($CH_3$)—, —$CH_2$—C($CH_3$)$_2$—$CH_2$—, —($CH_2$)$_4$—, —CH($CF_3$)—$CH_2$—, —CH($CH_2OH$)—$CH_2$—, —CH($CH_2NH_2$)—$CH_2$—, —CH($CH_2OCH_3$)—$CH_2$—, and the like.

Especially preferred compounds of Formula I compounds are those where L is —$CH_2$—, —$CH_2CH_2$— or —CH($CH_3$)—$CH_2$. Of course it is understood that where any substituent group has an asymmetric center e.g.

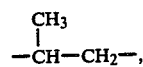

then all stereoisomers are included as mixtures or as separate isomers.

In the preferred embodiment, the

group is quaternized, monocyclic heteroaryl, substituted and unsubstituted, containing in addition to the quaternary N, up to 2 additional hetero atoms selected from O, N and S.

Representative useful monocyclic

groups are substituted and unsubstituted pyridinium, pyridazinium, pyrimidinium, pyrazinium, pyrazolium, triazolium, imidiazolium, thiazolium, oxazolium, isoxazolium and the like.

Preferred Formula I compounds are those where monocyclic

is a six membered heterocycle, such as substituted or unsubstituted pyridinium, pyridazinium or pyrazinium, and preferably substituted or unsubstituted pyridinium, wherein the substituents (one or more) are selected from OH, $NH_2$, $NHCH_3$, $OCH_3$, COO—$C_1$-$C_3$ alkyl, C(O)NHOH, phenyl, $N(CH_3)_2$, $C(O)CH_3$, $C(O)N(CH_3)OH$, $SO_3H$, $SCH_3$, CHO, COOH, $S(O)CH_3$, $SO_2CH_3$, $SO_2NH_2$, $SO_2NHCH_3$, CN, $C_5NH_2$, $CONH_2$, $CONH(CH_3)$, CH=N—OH, $C_1$-$C_6$ alkenyl and substituted and unsubstituted $C_1$-$C_6$ alkyl.

The preferred substituents are unsubstituted $C_1$-$C_6$ alkyl, $C_1$-$C_6$ alkenyl, and substituted $C_1$-$C_6$ alkyl wherein the substituents (one or more) are selected from OH, $NH_2$, $NHCH_3$, $OCH_3$, —COO—$C_1$-$C_3$alkyl, C(O)NHOH,

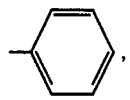

$N(CH_3)_2$, $C(O)CH_3$, C(O)—$N(CH_3)OH$, $SO_3H$, $SCH_3$, CHO, COOH, $S(O)CH_3$, $SO_2CH_3$, $SO_2NH_2$, $SO_2NHCH_3$, CN, $CSNH_2$, CH=N—OH, $CONH_2$, $CONH(CH_3)$.

Representative examples of preferred

pyridinium groups are those having the formulae

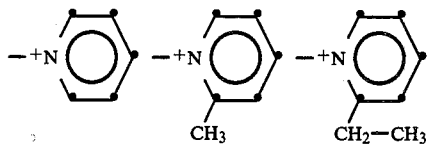

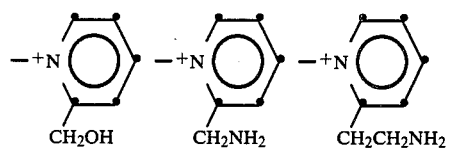

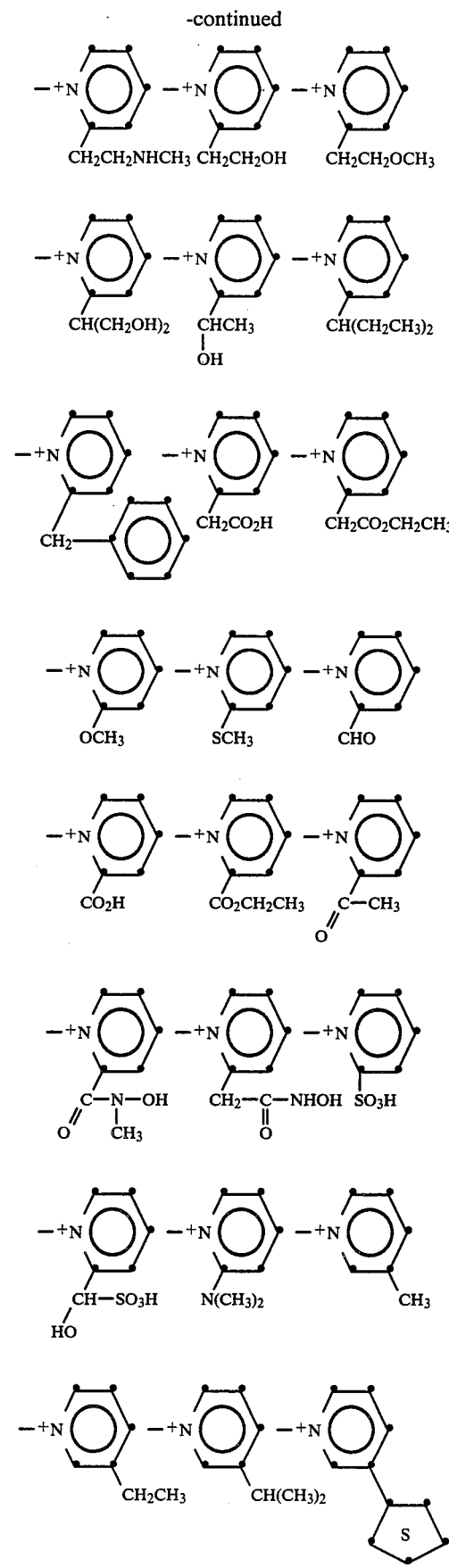

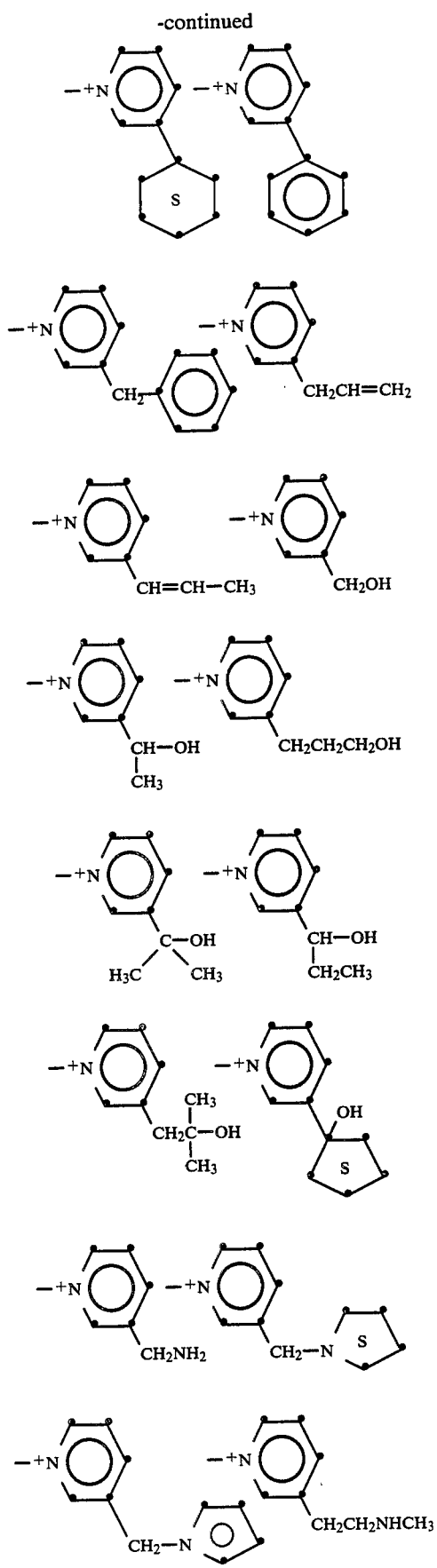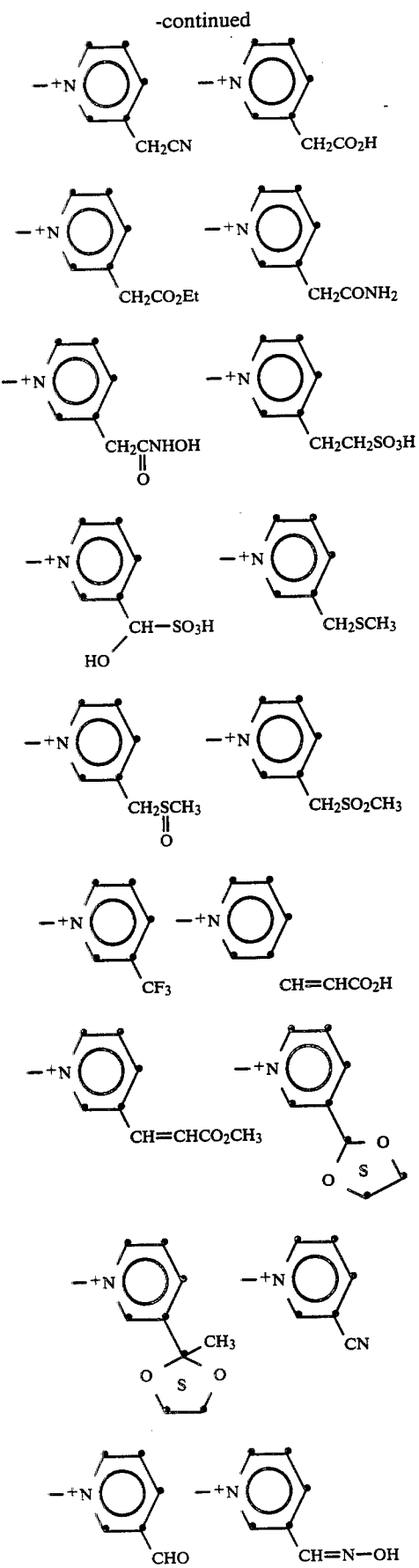

-continued
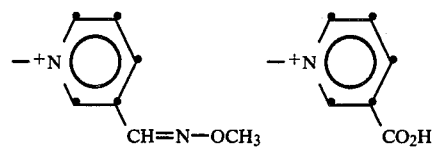
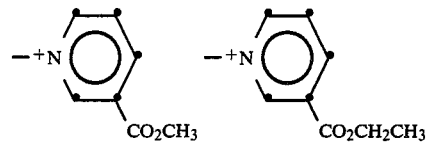
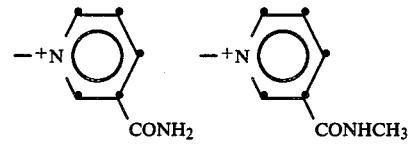
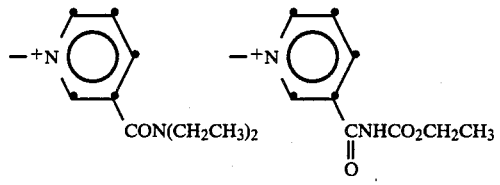
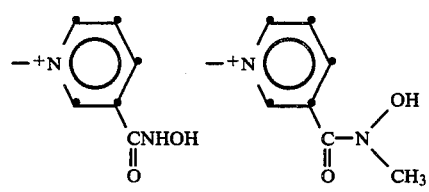
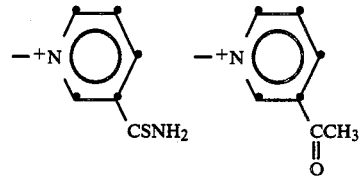
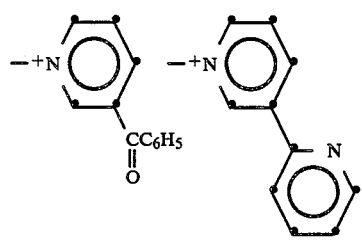
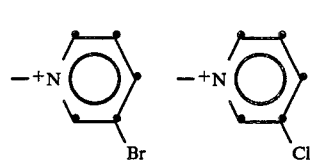
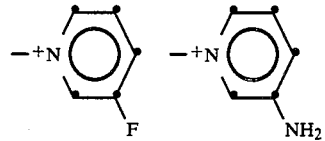
-continued
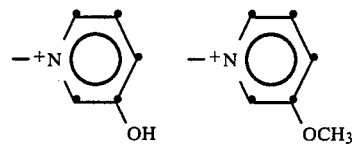
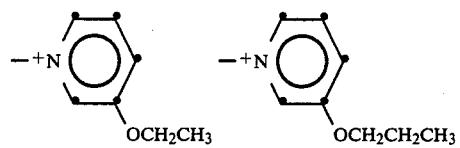
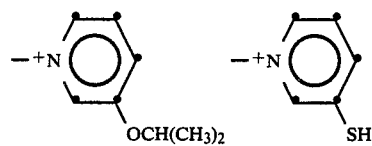
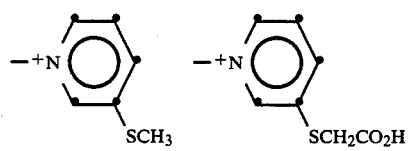
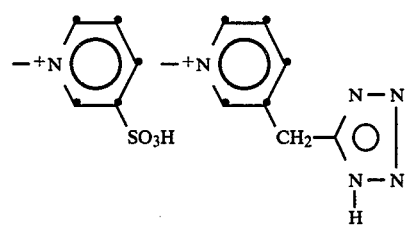
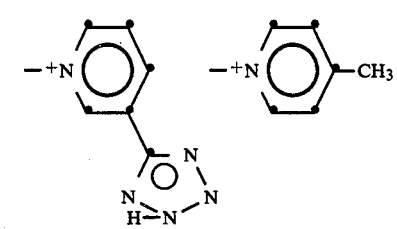
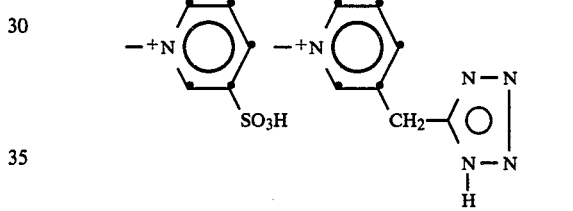
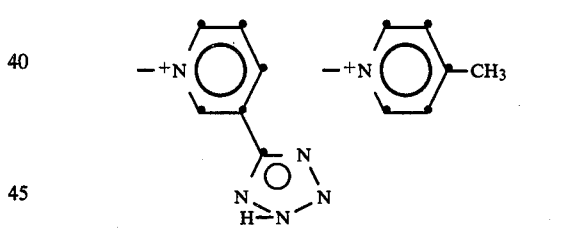
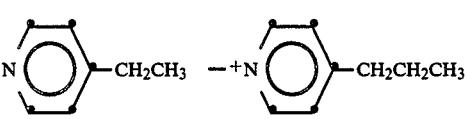
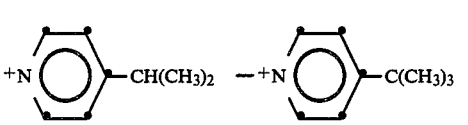
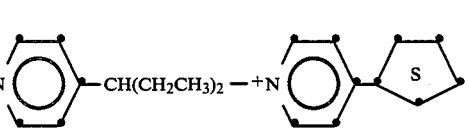
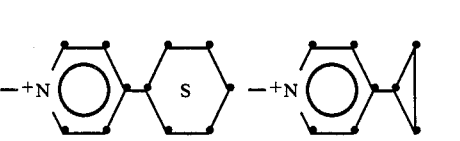

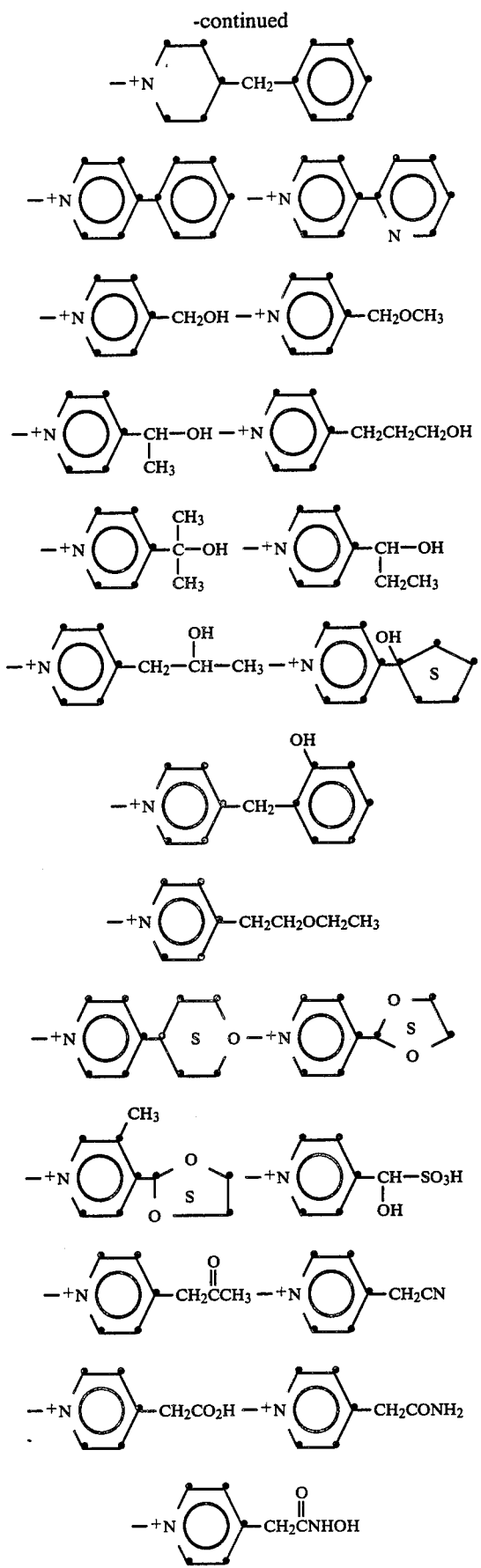
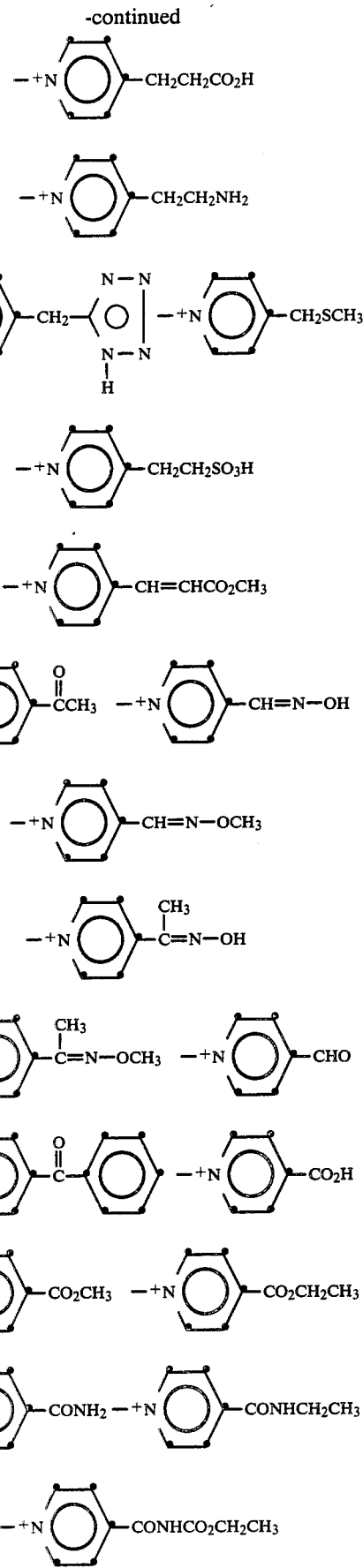

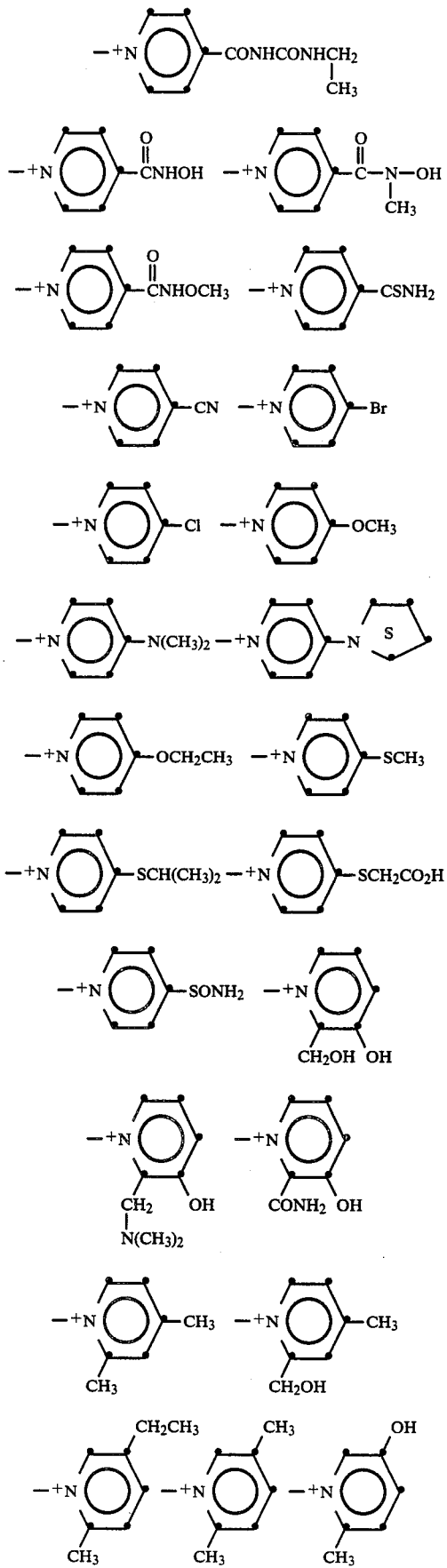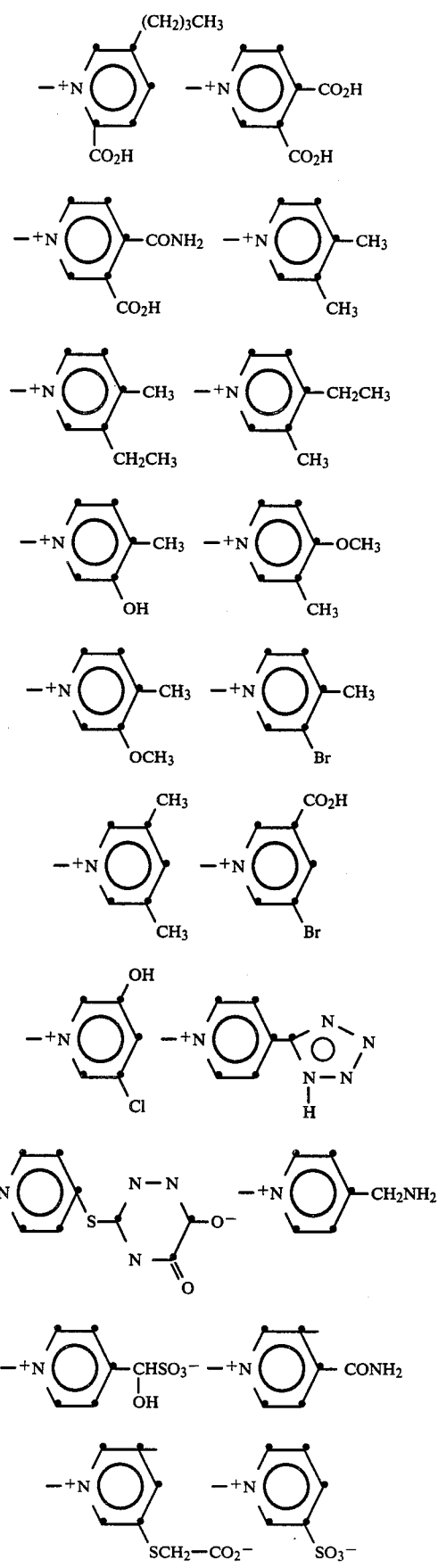

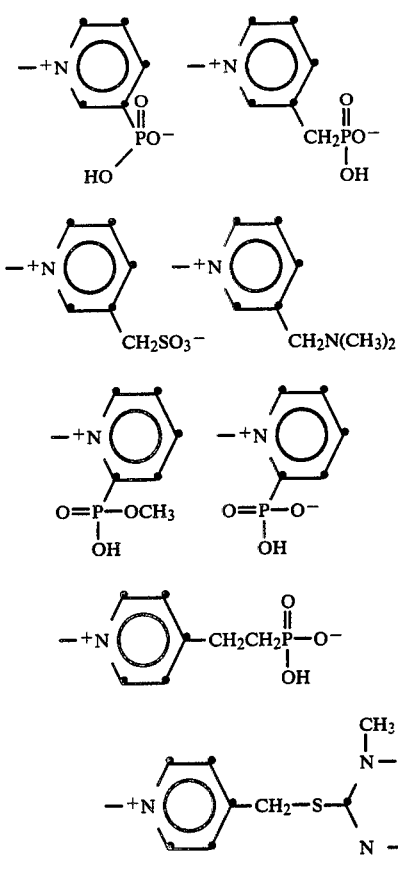

Representative examples of preferred monocyclic

other then pyridinium are those having the following formulae:

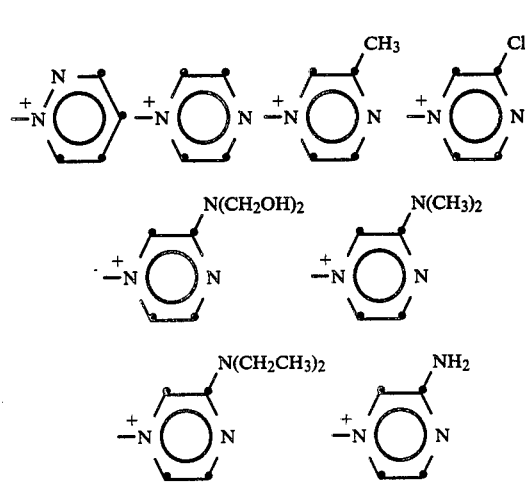

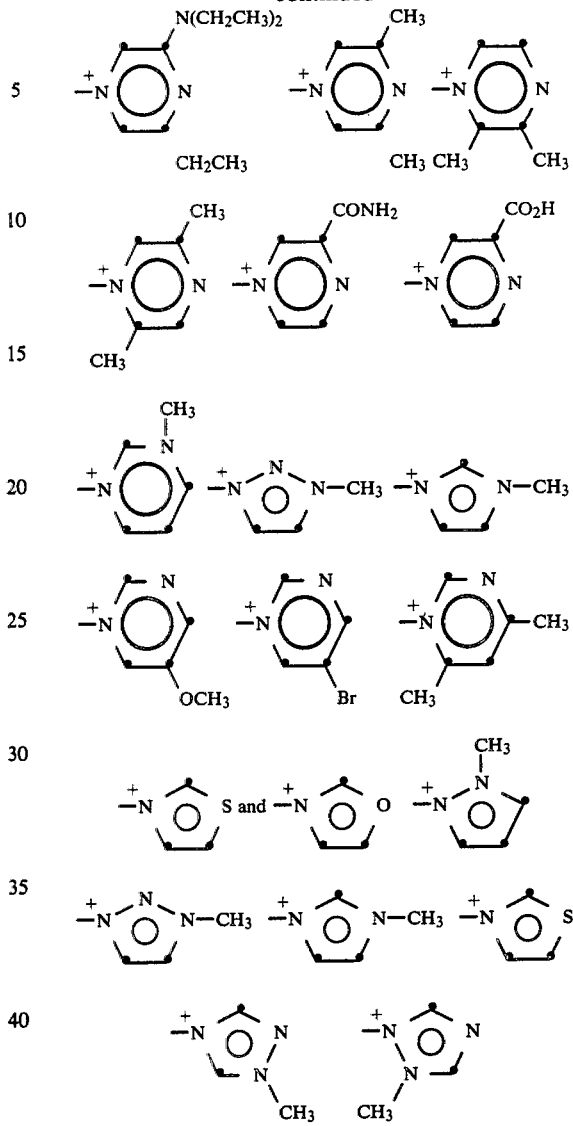

In another preferred embodiment, the —N+ group is a quaternized, bicyclic, substituted or unsubstituted heteroaryl, containing in addition to the quaternary N, up to 4 additional heteroatoms independently selected from O, N and S, and 9–10 total ring atoms.

Representative useful

groups are substituted and unsubstituted quinolinium, isoquinolinium, quinoxalinium, isocinolinium, thienopyridinium, furopyridinium, naphthyridinium, pyrazinopyridinium,

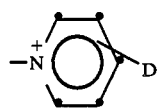

where D is a C$_{2-6}$ alkylene ring which may be interrupted by one or more O, S or N heteroatoms.

Preferred Formula I compounds are those where

is a bicyclic 9 or 10 membered ring, and more preferably substituted or unsubstituted quinolinium, isoquinolinium, or thienopyridinium.

The preferred substituents on the bicyclic heteroaryl groups are OH, C$_1$-C$_3$alkyl, NH$_2$, CH=NOCH$_3$, CF$_3$, halo, preferably Br or Cl, O—C$_1$-C$_3$alkyl, COOH, CHO, SO$_3$H, CONH$_2$, SO$_2$NH$_2$, N(C$_1$-C$_3$alkyl)$_2$, CH$_2$CO$_2$H, CH$_2$OH,

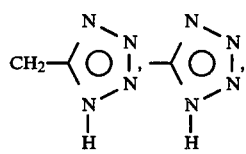

CH$_2$SO$_3$H, CN, CONH$_2$, CH$_2$CN, CH$_2$CONH$_2$, CH$_2$N(C$_1$-C$_3$alkyl)$_2$ and the like.

Representative examples of useful bicyclic

groups are:

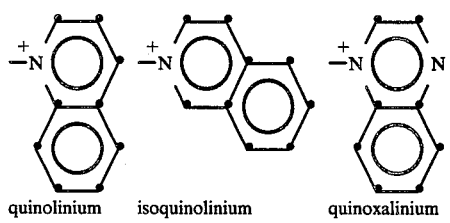

quinolinium    isoquinolinium    quinoxalinium

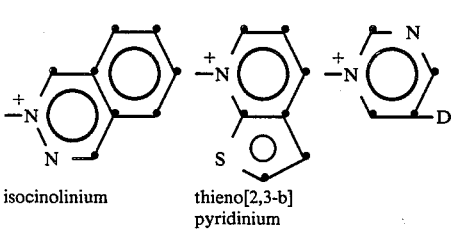

isocinolinium    thieno[2,3-b] pyridinium

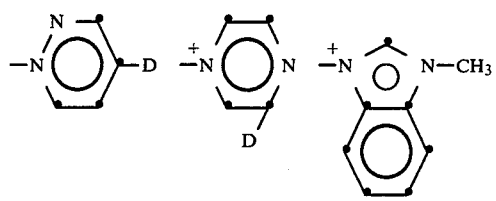

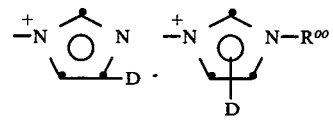

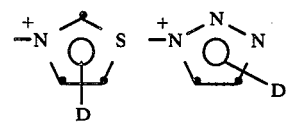

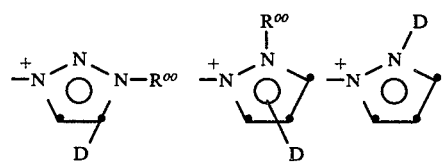

where R$^{\circ\circ}$ is unsubstituted or substituted C$_1$-C$_4$alkyl and D is C$_3$-C$_5$alkylene.

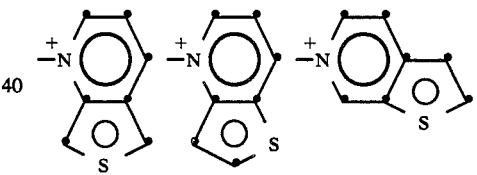

thieno[3,4-b]    thieno[3,2-b]    thieno[2,3-c]
pyridinium    pyridinium    pyridinium

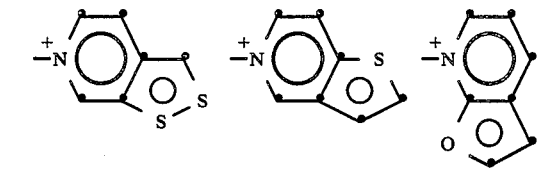

thieno[3,4-c]    thieno[3,2-c]    furo[2,3-b]
pyridinium    pyridinium    pyridinium

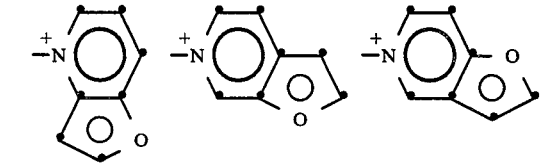

furo[3,2-b]    furo[2,3-c]    furo[3,2-c]
pyridinium    pyridinium    pyridinium -continued
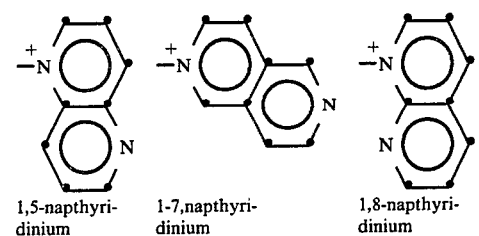
1,5-napthyridinium   1-7,napthyridinium   1,8-napthyridinium
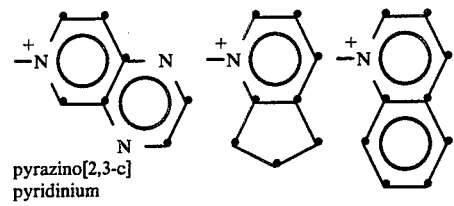
pyrazino[2,3-c]pyridinium
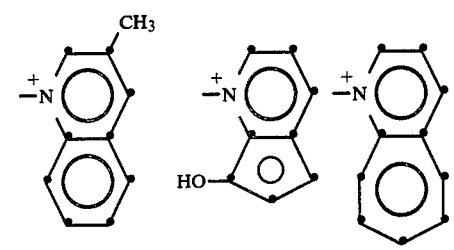
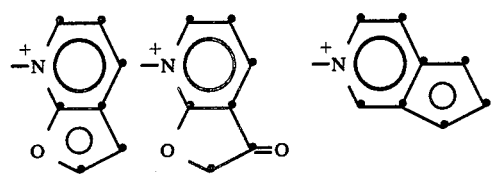
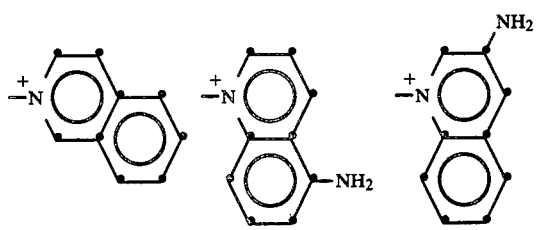
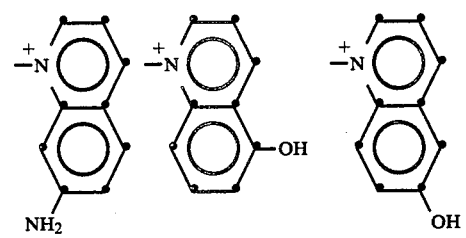
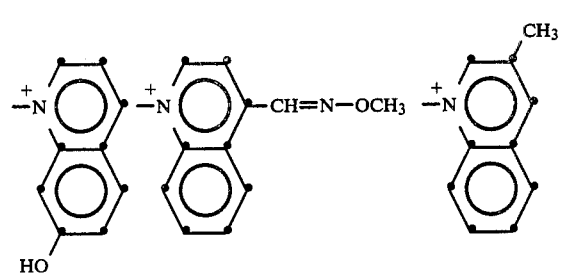
-continued
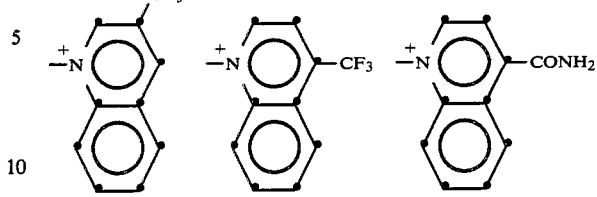
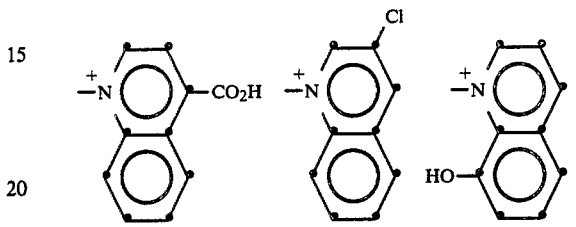
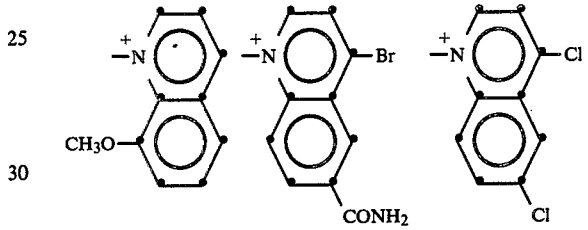
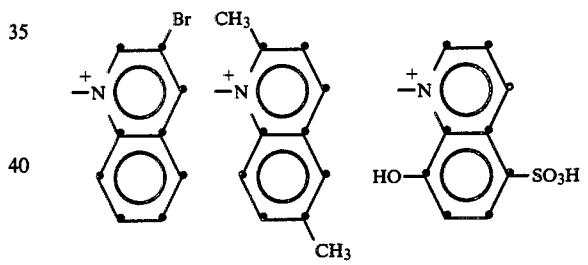
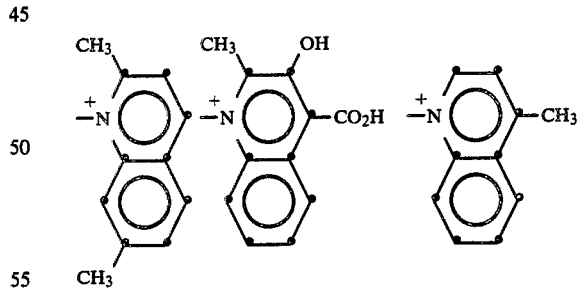
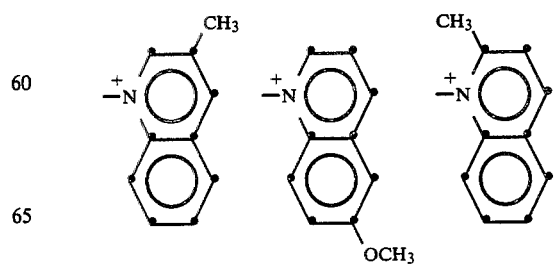

-continued
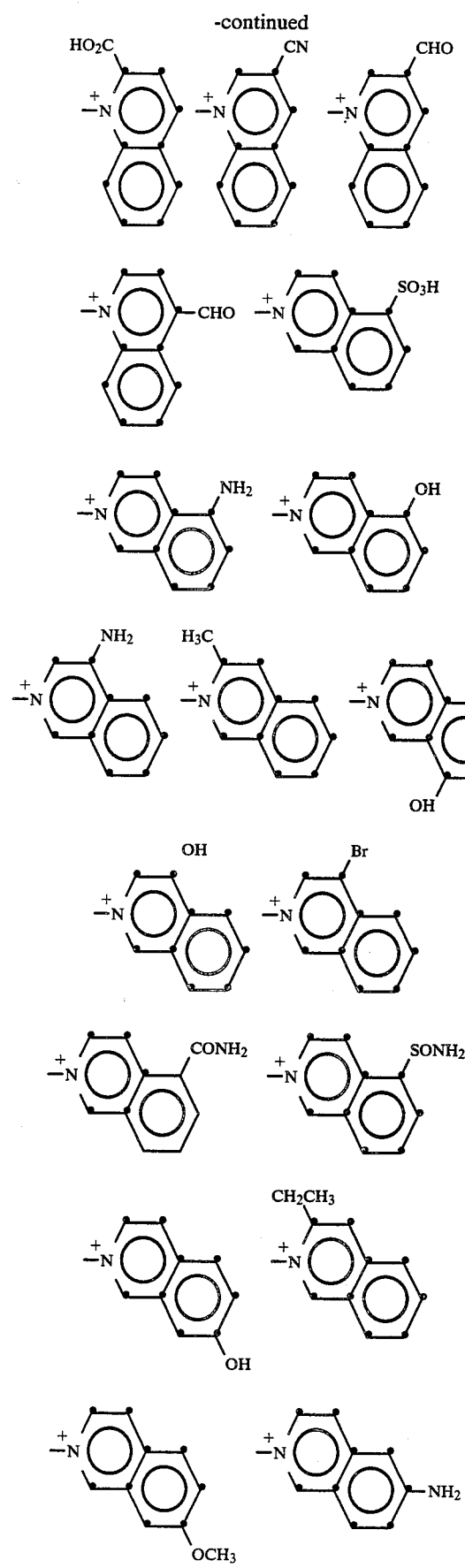
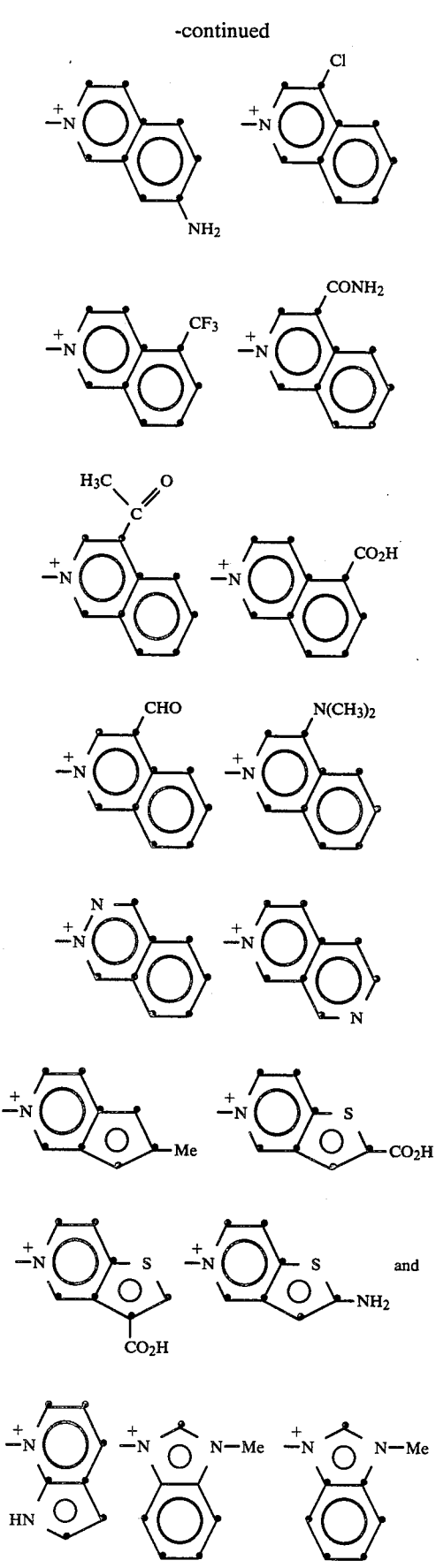

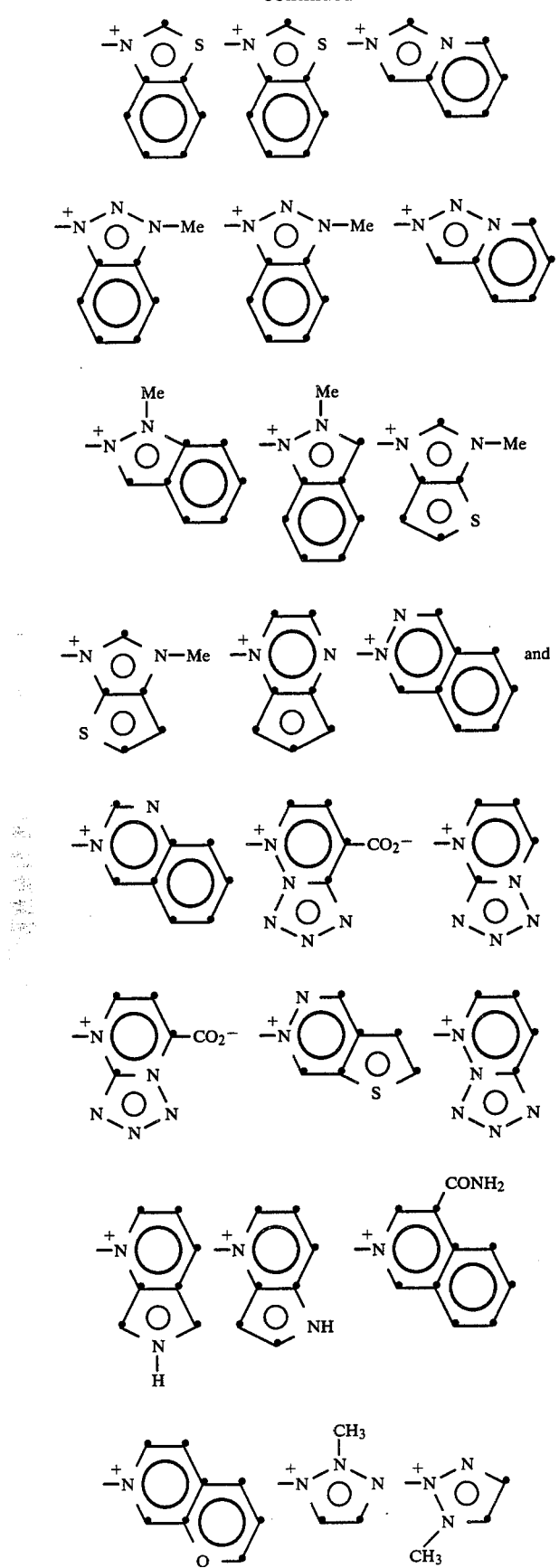
Preferred embodiments of the internally alkylated subject composition are given by the following formula and table listing the specific substituent.
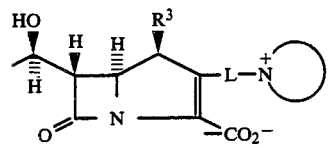
The compounds of Formula I include inner (Zwitterion) salts when Y is COO⁻, eg.
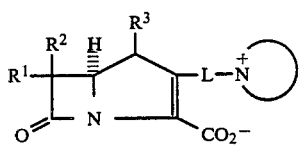
or, when Y is other than COO⁻, salts with an external, physiologically acceptable counterion, $Z^-$, eg.

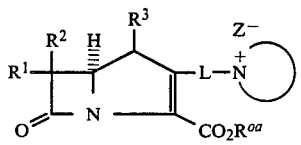

$R^{oa}$ is a pharmaceutically acceptable ester, eg., pivaloyloxymethyl, phthalidyl, phtalimidomethyl, acetoxymethyl, ethoxycarbonyloxyethyl, pivaloyloxyethyl, 4-methyl-2-oxo-1,3-dioxolen-5-yl-methyl or salt group; and $Z^-$ is $Cl^-$, $Br^-$, $I^-$, $OH^-$, $H_2O_3^-$, $CH_3CO_2^-$ and the like. The inner salts are preferred.

Compounds of Formula I include the stereoisomers as mixtures and as separate isomers.

Compounds having the stereochemistry shown below are preferred:

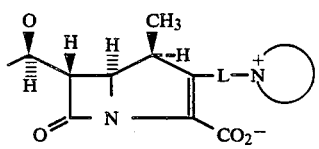

where

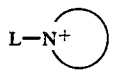

contains a chiral center, the side chain chirality leads to diastereometric products. The products can be separated by conventional methods, used as mixtures, or synthesized stereospecifically.

The compounds of the present invention are valuable antibiotics, active against various Gram-positive and Gram-negative bacteria and accordingly find utility in human and veterinary medicine. Representative pathogens which are sensitive to antibiotics I include: *Staphyloccus aureus, Escherichia coli, Klebsiella Pneumoniae, Bacillus subtilis, Salmonella typhosa, Pseudomonas* and *Bacterium proteus*. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in water-based paints and in the white water of paper mills to inhibit the growth of harmful bacteria.

The compounds of this invention may be used in any of a variety of pharmaceutical preparations. They may be employed in capsule, powder form, in liquid solution, or in suspension. They may be adminstered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg of body weight of the subject in one or more treatments per day. A preferred daily dosage for adult humans lies in the range of from about 10 to 240 mg of active ingredient per kg of body weight. Another factor influencing the precise dosage regimen, apart from the nature of the infection and peculiar identity of the individual being treated, is the molecular weight of the chosen species of this invention (I).

The compositions for human delivery per unit dosage, whether liquid or solid, may contain from 0.1% to 99% of active material, the preferred range being from about 10–60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the formula I antibiotic is parenteral by i.v. infusion, i.v. bolus, or i.m. injection.

For adults, 5–50 mg of Formula I antibiotic per kg of body weight given 2, 3, or 4 times per day is preferred. Preferred dosage is 250 mg to 1000 mg of the Formula I antibiotic given two (b.i.d.) three (t.i.d.) or four (q.i.d.) times per day. More specifically, for mild infections, and particularly urinary tract infections, a dose of 250 mg t.i.d. or q.i.d. is recommended. For moderate infections against highly susceptible gram positive and gram negative organisms, a dose of 500 mg t.i.d. or q.i.d. is recommended. For severe, life-threatening infections against organisms at the upper limits of sensitivity to the antibiotic, a dose of 1000 t.i.d. or q.i.d. is recommended.

For children, a dose of 5–25 mg/kg of body weight given 2, 3, or 4 times per day is preferred; a dose of 10 mg/kg t.i.d. or q.i.d. is usually recommended.

Antibiotic compounds of Formula I are of the broad class known as carbapenems or 1-carbadethiapenems. Certain of these carbapenems are susceptible to attack by a renal enzyme known as dehydropeptidase (DHP). This attack or degradation may reduce the efficacy of the carbapenem antibiotic. Inhibitors of DHP and their use with carbapenem antibiotics are disclosed in the prior art [see published European Patent Applications No. 79102616.4 filed July 24, 1979 (Pat. No. 10573); 79102615.6, filed July 24, 1979 (application No. 15573); and No. 82107174.3, filed Aug. 9, 1980 (application No. 72014)].

The present I compounds may, where DHP inhibition is desired or necessary, be combined or used with the appropriate DHP inhibitor as described in the aforesaid published applications. Thus, to the extent that the cited European patent applications 1.) define the procedure for determining DHP susceptibility of the present carbapenems and 2.) disclose suitable inhibitors, combination compositions and methods of treatment, they are incorporated herein by reference. A preferred weight ratio of I compound:DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

These combination compositions and their use is another embodiment of the present invention.

The compounds of Formula I may be prepared by any convenient process.

METHODS OF PREPARATION (1) L = —CH$_2$, —CH(CH$_3$)—

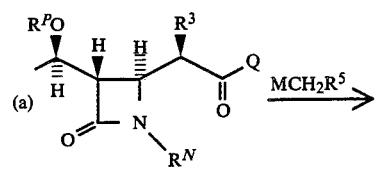

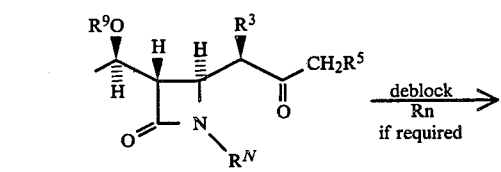

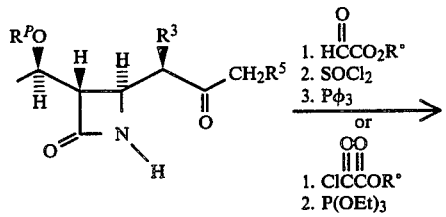

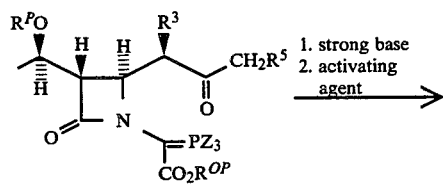

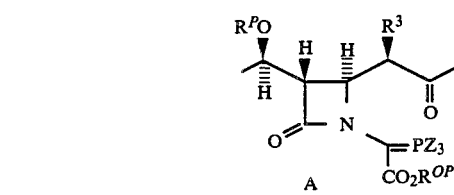

FURTHER ELABORATION OF A

Option 1. (X = OH)

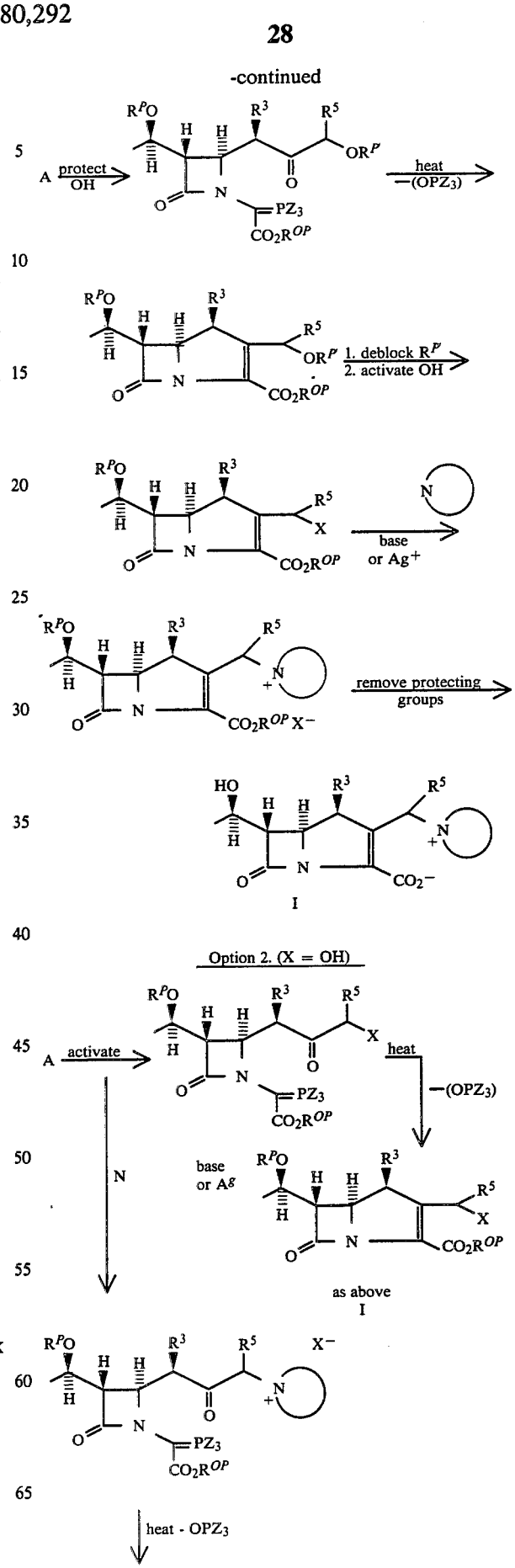

-continued

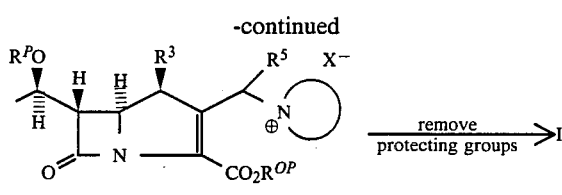 $\xrightarrow{\text{remove protecting groups}}$ I

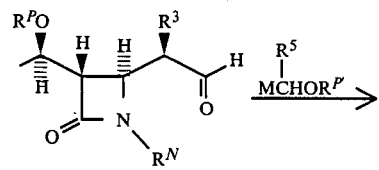 $\xrightarrow{\text{MCHOR}^P}$

ALTERNATE PREPARATIONS OF A

1.

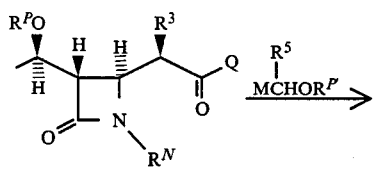 $\xrightarrow{\text{MCHOR}^P}$

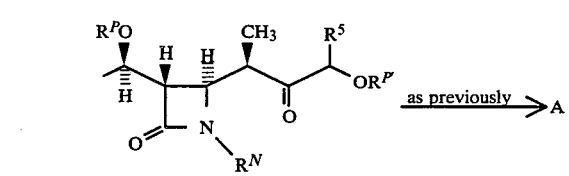 $\xrightarrow{\text{as previously}}$ A

2.

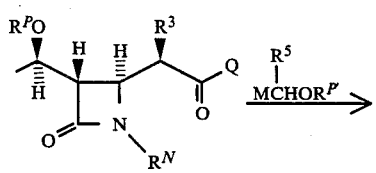 $\xrightarrow{\text{MCHOR}^P}$

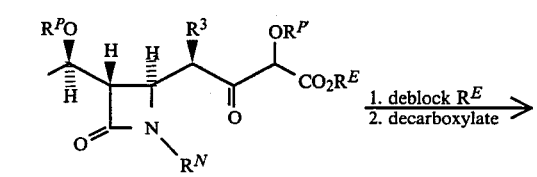 $\xrightarrow{\text{1. deblock } R^E}{\text{2. decarboxylate}}$

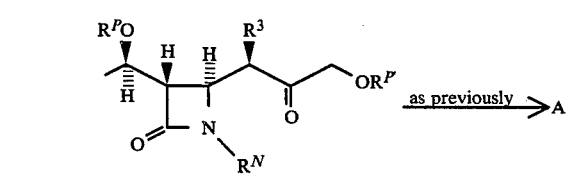 $\xrightarrow{\text{as previously}}$ A

3.

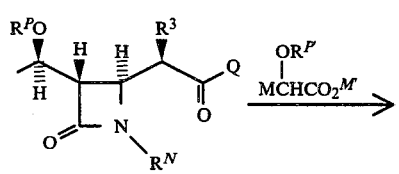 $\xrightarrow{\text{MCHCO}_2 M'}$

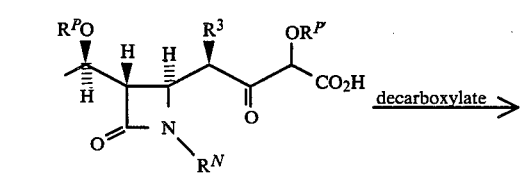 $\xrightarrow{\text{decarboxylate}}$

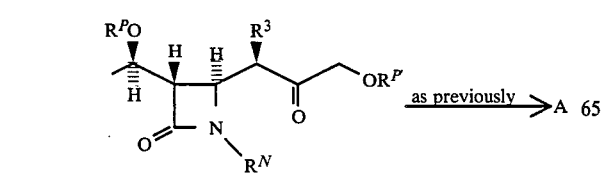 $\xrightarrow{\text{as previously}}$ A

-continued

4.

[Structure with aldehyde] $\xrightarrow{\text{MCHOR}^P}$

[Structure with OH] $\xrightarrow{[O]}$

[Structure] $\xrightarrow{\text{as above}}$ A

Option 3. (X = Cl, Br, I, etc.)

$A \xrightarrow[\text{or Ag}^+]{\text{base}}$

[Structure with X⁻] $\xrightarrow{\text{as above}}$ I heat

[Structure] $\xrightarrow{\text{as above}}$ I

Q = —S—pyridyl, —O—phenyl, —S—phenyl,

—Cl, —Br, —N(imidazolyl)

or the like;
$R^5 = CH_3$, H;
M, M' = Li, Cu, MgX, Zn, Na or the like;
X, $R^3$ = as defined previously;
$R^{OP}$ = as defined previously;
$R^P$, $R^{P'}$ = triorganosilyl, allyloxycarbonyl, p-nitrobenzoyloxylcarbonyl, etc.;
strong base = LiNiPr₂, LiN(TMS)₂,

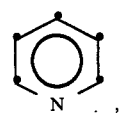

KH, etc.;
Z=

,

—OEt;

activating agent=$O_2$, MoOPH, $Cl_2$, $Br_2$, $I_2$, $BrSO_2Ar$, etc.;

activating agent (OH)=$ClSO_2CH_3$, $ClSO_2Ar$, TMSI, $\phi P_3/CCl_4$ etc., possilby followed by displacement with halogen;

$R^N$=triorganolsilyl,

(2)

$L =$ —$CH_2CH_2$—, —$\overset{CH_3}{C}HCH_2$—, —$CH_2\overset{CH_3}{C}H$—, —$(CH_2)_3$—, —$\overset{CH_3}{C}HCH_2CH_2$—, —$CH_2\overset{CH_3}{C}HCH_2$—, —$CH_2CH_2\overset{CH_3}{C}H$—, etc. $C_6$ (a)

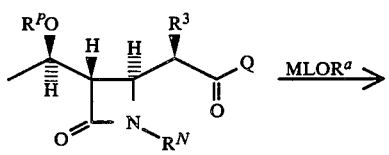 $\xrightarrow{MLOR^a}$

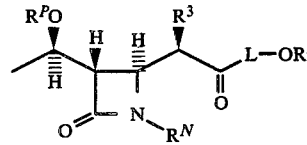

(If $R^N$ = Wittig side chain, then) heat (If $R^N$ = protecting group, then) 1. remove $R^N$

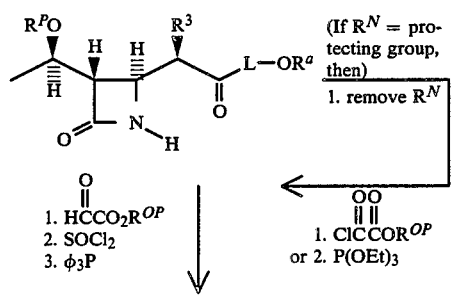

1. $HCCO_2R^{OP}$
   $\overset{O}{\|}$
2. $SOCl_2$
3. $\phi_3P$

1. $ClCCOR^{OP}$
   $\overset{OO}{\|\|}$
   or 2. $P(OEt)_3$

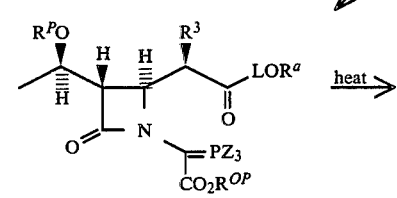

$\xrightarrow{heat}$

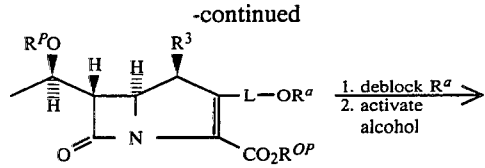 $\xrightarrow[\text{2. activate alcohol}]{\text{1. deblock } R^a}$

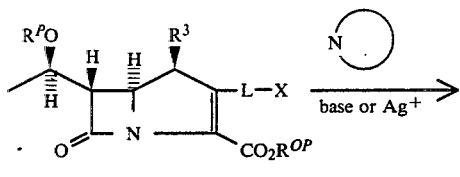 $\xrightarrow{\text{base or Ag}^+}$

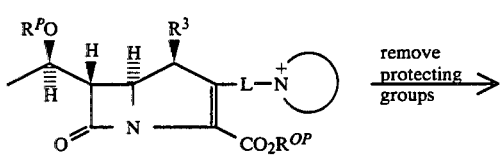 $\xrightarrow{\text{remove protecting groups}}$

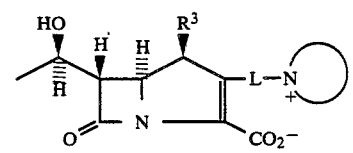

I (b)

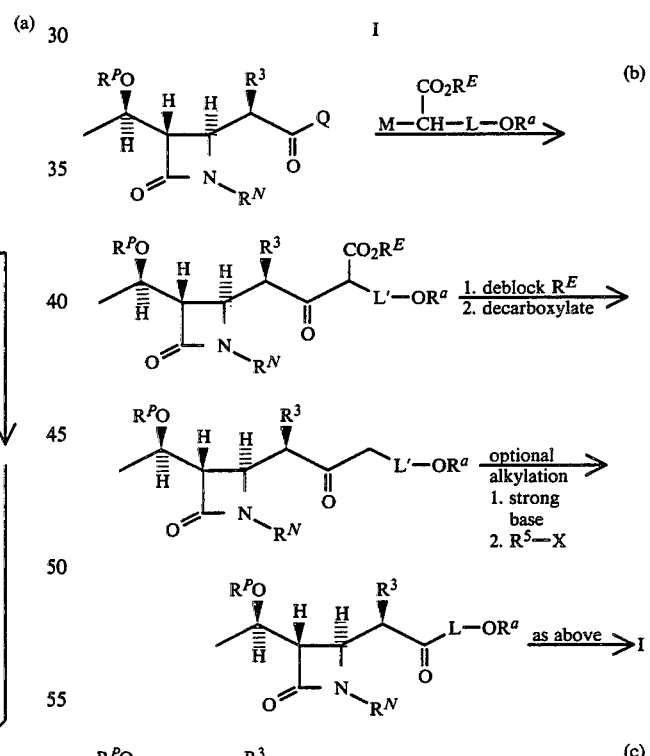

(c)

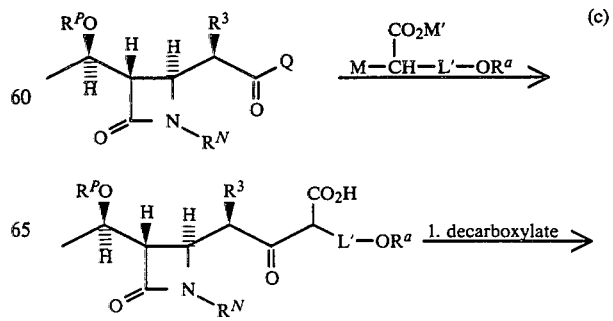

-continued

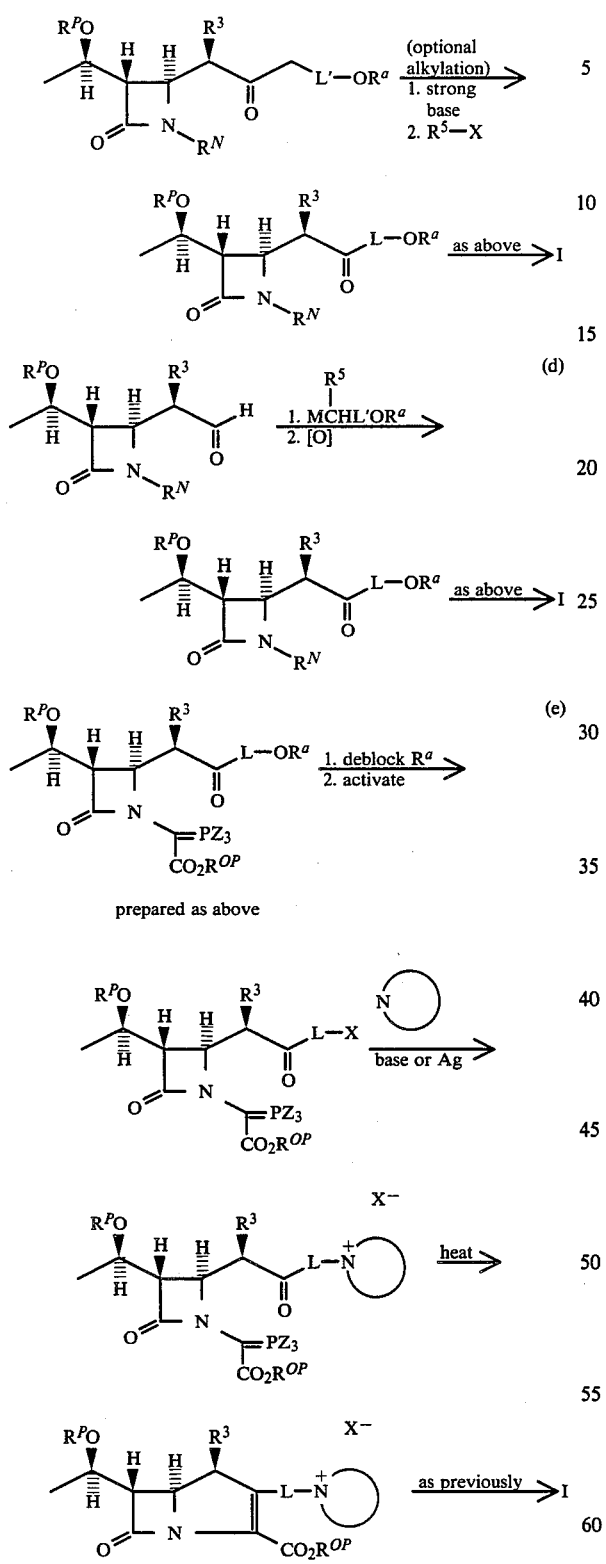

prepared as above

All variables are as defined above.

The following examples illustrate the preparation of compounds of Formula I. The temperature is in degrees Celsius unless otherwise indicated.

EXAMPLE 1

Preparation of (1R,5S,6S,8R)-2-[[[1-methyl-1H-tetrazol-5-yl]-thio]-methyl]-6-(hydroxyethyl)-1-methylcarbapen-2-em-3-carboxylic acid, potassium salt, 6

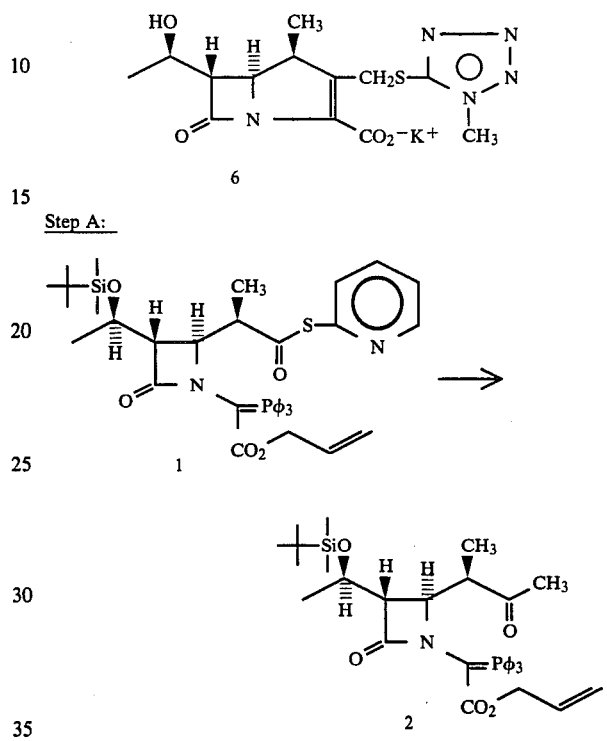

Step A:

A commercial sample of 3M methylmagnesium bromide in ether (690 1, 2.07 mmol) is added dropwise to a stirred solution of thiopyridyl ester 1 (1.06 g, 1.41 mmol) in anhydrous tetrahydrofuran (25 ml) at −78° under nitrogen. After 5 minutes, work-up of a small aliquot shows on TLC the less polar product as well as residual starting material. An additional amount of methyl magnesium bromide (140 1, 0.42 mmol) is added, and stirring is continued at −78° for 10 minutes. The reaction mixture is then added to a saturated NH₄Cl solution (35 ml), H₂O (10 ml), and ethyl acetate (40 ml). After phase separation, the aqueous layer is extracted with an additional amount of ethyl acetate. The combined organic layers are washed with cold 1N HCl (35 ml), cold 10% NaHCO₃ (35 ml), and then brine (35 ml). After drying over MgSO₄, the organic layer is concentrated in vacuo to a yellow foam. Chromatography on Baker's silica gel (eluting with 0 10% ethyl acetate in methylene chloride) affords ca. 90% pure methyl ketone (800 mg). Preparative thin layer chromatography on silica gel (eluting with 1:1 ethyl acetate-hexane and extracting with 1:1 ethyl acetate-methylene chloride) provides pure methyl ketone 2 (650 mg, 70% yield).

NMR (CDCl₃) selected absorbances: 8.0–7.4 (aromatic protons), 6.0 (m, —CH₂C$\underline{H}$=CH₂), 2.2

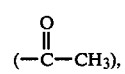

0.8 (—C(CH₃)₃) in ppm downfield from TMS.

IR (CH$_2$Cl$_2$ solution) 1750, 1720, 1650, 1625 cm$^{-1}$.
MS (FAB) 658 (M+1).

EXAMPLE 2

Alternate Preparation of Intermediate 3

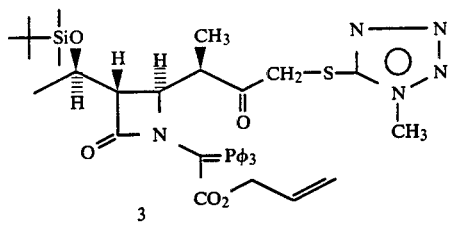
3

Step A:

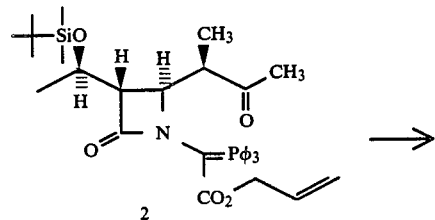
2

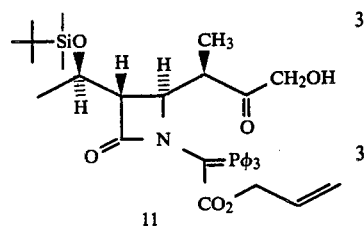
11

To diisopropyl amine (12 £1, 0.087 mmol) in tetrahydrofuran (1 ml) at 0° under nitrogen is added 1.3M BuLi in hexane (67 £1, 0.087 mmol). After 10 minutes at 0° the temperature is lowered to −78°, and a solution of methyl ketone 2 (38 mg, 0.058 mmol) in tetrahydrofuran (500 £1) is added. Following stirring 3 minutes at −78°, MoO$_5$ pyridine HMPA (MoOPH) (38 mg, 0.088 mmol) is added. The temperature is raised and held at −30° for 30 minutes. Upon addition of a saturated Na$_2$SO$_3$ solution (600 £1), 1M KH$_2$PO$_4$ (240 £1), water (2 ml) and ethyl acetate (2 ml) the cooling bath is removed, and the reaction mixture is stirred vigorously for 15 minutes. After phase separation, the aqueous layer is re-extracted with ethyl acetate. The combined organic layers are washed with brine, dried over MgSO$_4$ and concentrated to give a green oil (47 mg). Preparative thin layer chromatography on silica gel (plate eluted with 1:1 ethyl acetate-hexane and extracted with 1:1 ethyl acetate-methylene chloride) provides recovered starting material (10 mg) and the hydroxymethyl ketone 11 (13 mg, 32% yield).

NMR (CDCl$_3$) selected absorbances 8–7.4 (aromatic protons), 6.0 (m, —CH$_2$CH=CH$_2$), 4.4 (m, CH$_2$OH), 0.8 (C(CH$_3$)$_3$) in ppm downfield from TMS.

IR (CH$_2$Cl$_2$ solution) 1755, 1725, 1650, 1625 cm$^{-1}$.
MS (FAB) 674 (M+1), 262 ($\phi_3$P).

EXAMPLE 3

Preparation of Allyl (1R,5S,6S,8R)-2-hydroxymethyl-6-(1-t-butyldimethylsilyloxyethyl)-1-methylcarbapen-2-em-3-carboxylate

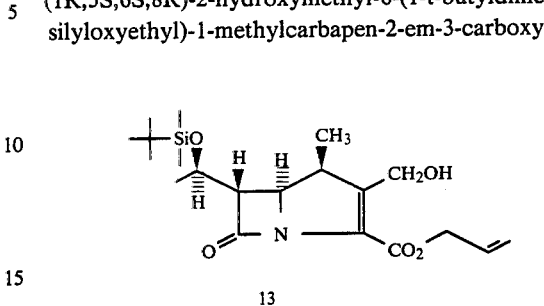
13

Step A:

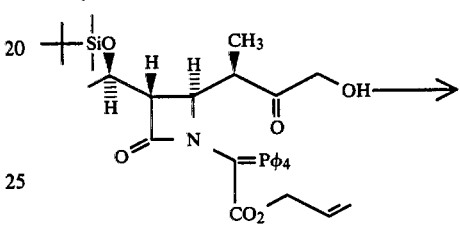
11

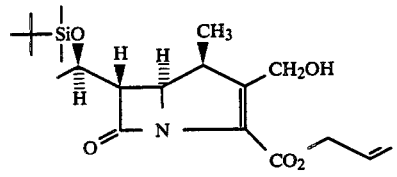
13

A solution of 11 (12 mg, 0.018 mmol) in toluene (1 ml) is heated at reflux under nitrogen for one hour and then concentrated to a colorless oil. Preparative thin layer chromatography on silica gel (plate eluted with 1:1 ethyl acetate-hexane and extracted with 1:1 ethyl acetate-methylene chloride) gives the carbapenem 13 (5 mg, 70% yield).

NMR (CDCl$_3$) 5.98 (m, —CH$_2$CH=CH$_2$), 5.38 (m, CH$_2$CH=CH$_2$), 4.80 (m, —CH$_2$CH=CH$_2$), 4.47 (m, CH$_2$OH), 4.22 (m, H$_5$+H$_8$), 3.25 (m, H$_1$, H$_6$+OH), 1.26 and 1.21 (sd, 1—CH$_3$ and CH$_3$CHO—), 0.9 (C(CH$_3$)$_3$), 0.07 (Si(CH$_3$)$_2$) in ppm downfield from TMS.

IR (CH$_2$Cl$_2$ solution) 1775, 1710 cm$^{-1}$.
UV (dioxane) max=283 nm/MS (FAB).

EXAMPLE 4

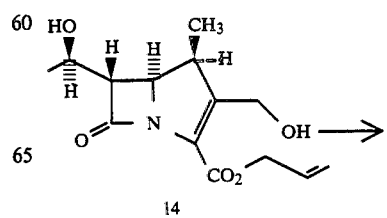
14

-continued

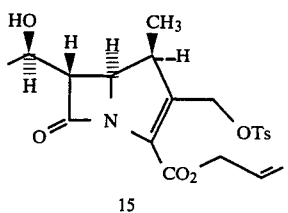
15

Step A

A solution of dihydroxycarbapenem 14 (48 mg, 0.18 mmol) and p-toluene sulfonic anhydride (55 mg, 0.18 mmol) in anhydrous methylene chloride (5 ml) is cooled to 0° C. and triethylamine (20 mg, 0.20 mmol) is added slowly by syringe. The resulting solution is stirred at 0° C. for 1 hr, then is diluted with methylene chloride (20 ml) and washed quickly with cold pH 7 phosphate buffer and brine. The organic phase is dried over anhydrous sodium sulfate and the solvent is removed in vacuo to provide crude tosylate 15 which is carried on without further purification.

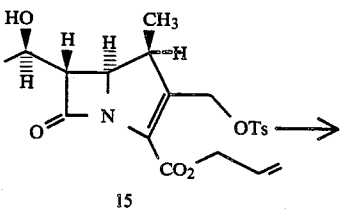
15

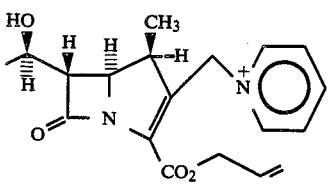
16

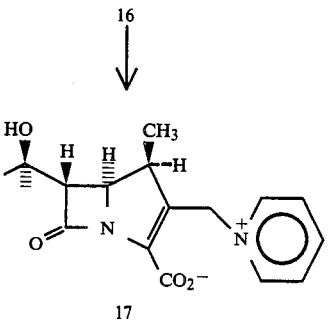
17

Step B

An ice cold solution of tosylate 15 (84 mg, 0.20 mmol) in anhydrous acetonitrile (5 ml) is treated with pyridine (40 mg, 0.50 mmol). The mixture is stirred at 0° C. for 15 min., then allowed to warm to room temperature. After standing three hours the solution is concentrated in vacuo to give crude 16. This material is suspended in a mixture of methylene chloride (2 ml) and ethyl acetate (2 ml). To this mixture is added a solution of potassium ethylhexanoate in ethyl acetate (0.40 ml of 0.5M solution, 0.20 mmol), triphenylphosphine (3.4 mg, 0.014 mmol) and tetrakis(triphenylphosphine)palladium[0] (0.5 mg, 0.0005 mmol). The reaction mixture is stirred under nitrogen at ambient temperature for 2 hr., then is concentrated in vacuo. The residue is partitioned between water (5 ml) and ethyl ether (5 ml). The aqueous phase is separated and washed with an additional portion of ether, then is concentrated in vacuo and chromatographed on two RPS plates (eluting with ethanol/water). The U.V. active band is removed from the plates and extracted with 4:1 acetonitrile/water. This solution is washed four times with hexanes, then concentrated in vacuo and lyophilized to yield compound 17.

EXAMPLE 5

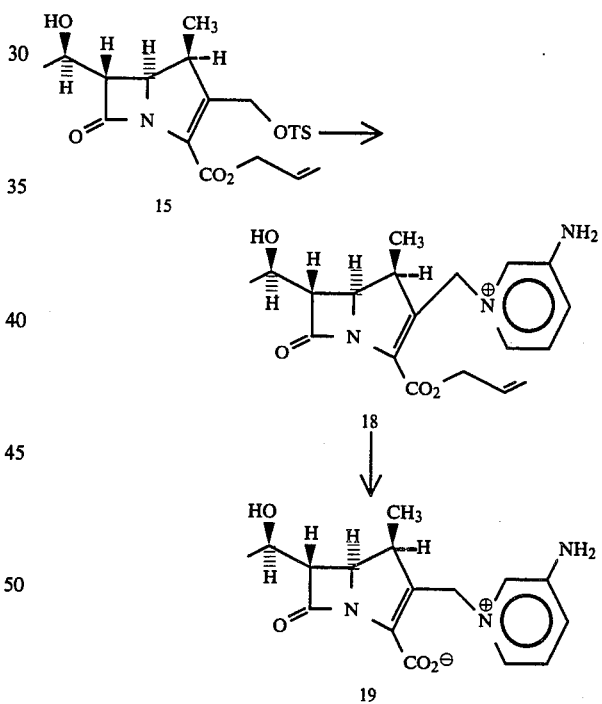

An ice cold solution of tosylate 15 (84 mg, 0.20 mmol) in anhydrous acetonitrile (5 ml) is treated with 3-aminopyridine (25 mg, 0.26 mmol). The mixture is stirred at 0° C. for 15 min., then allowed to warm to room temperature. After standing three hours the solution is concentrated in vacuo to give crude 18. This material is suspended in a mixture of methylene chloride (2 ml) and ethyl acetate (2 ml). To this mixture is added a solution of potassium ethylhexanoate in ethyl acetate (0.40 ml of 0.5M solution, 0.20 mmol), triphenylphosphine (3.4 mg, 0.014 mmol) and tetrakis(triphenylphosphine)palladium[0] (0.5 mg, 0.0005 mmol). The reaction mixture is stirred under nitrogen at ambient temperature

EXAMPLE 7

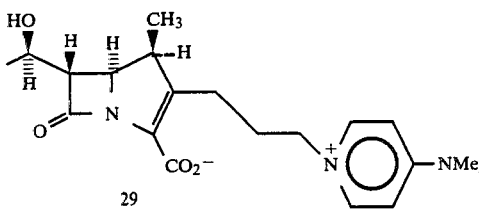

29

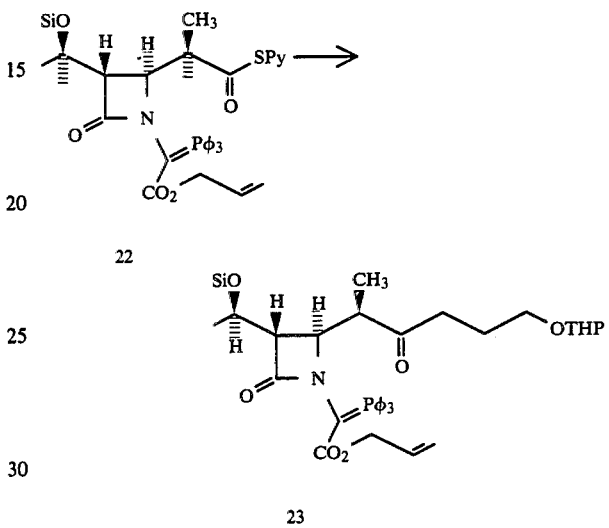

22

23

EXAMPLE 6

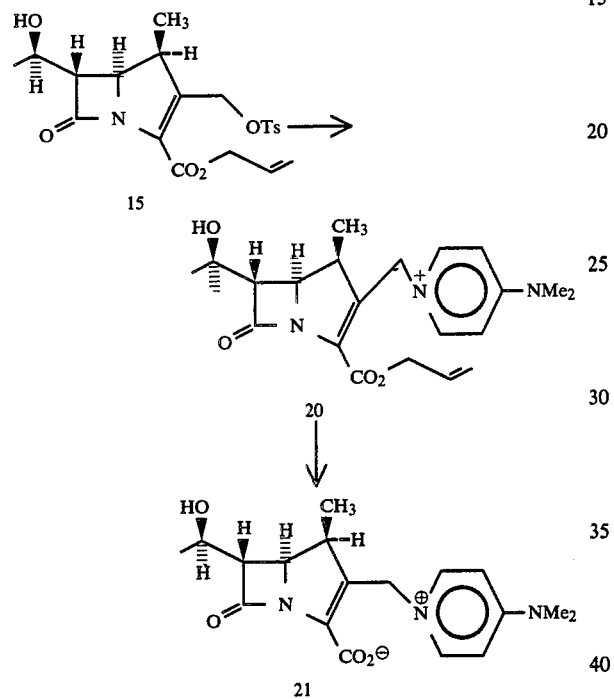

15

20

21

An ice cold solution of tosylate 15 (84 mg, 0.20 mmol) in anhydrous acetonitrile (5 ml) is treated with 4-dimethylaminopyridine (25 mg, 0.20 mmol). The mixture is stirred at 0° C. for 15 min., then allowed to warm to room temperature. After standing three hours the solution is concentrated in vacuo to give crude 20. This material is suspended in a mixture of methylene chloride (2 ml) and ethyl acetate (2 ml). To this mixture is added a solution of potassium ethylhexanoate in ethyl acetate (0.40 ml of 0.5M solution, 0.20 mmol), triphenylphosphine (3.4 mg, 0.014 mmol) and tetrakis(triphenylphosphine)palladium[0] (0.5 mg, 0.0005 mmol). The reaction mixture is stirred under nitrogen at ambient temperature for 2 hr., then is concentrated in vacuo. The residue is partitioned between water (5 ml) and ethyl ether (5 ml). The aqueous phase is separated and washed with an additional portion of ether, then is concentrated in vacuo and chromatographed on two RPS plates (eluting with ethanol/water). The U.V. active band is removed from the plates and extracted with 4:1 acetonitrile/water. This solution is washed four times with hexanes, then concentrated in vacuo and lyophilized to yield compound 21.

Step A

A solution of 1-bromo-3-(tetrahydropyranyloxy)propane (443 mg, 2.0 mmol) in 4.0 ml of tetrahydrofuran is treated with magnesium (50 mg, 2.0 mmol) to form the Grignard reagent and the resulting solution added dropwise to a solution of pyridylthioester 22 (1.0 g, 1.4 mmol) in anhydrous tetrahydrofuran (25 ml) at −78° C. under dry nitrogen. After one hour the reaction mixture is added to saturated ammonium chloride solution (35 ml), water (10 ml) and ethyl acetate (40 ml). The phases are separated and the aqueous layer is extracted with an additional portion of ethyl acetate (15 ml). The combined organic layers are washed with cold 1N hydrochloric acid solution, cold 10% aqueous sodium bicarbonate solution, water and brine. After drying over anhydrous magnesium sulfate the organic phase is concentrated in vacuo and the residual gum is chromatographed on silica gel (eluting with 0–10% ethyl acetate in methylene chloride) to yield ketone 23.

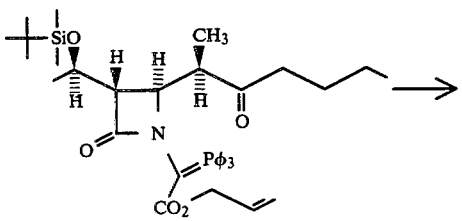

23

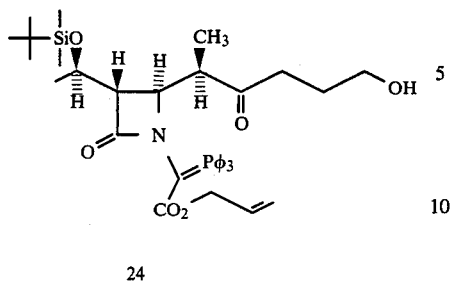

24

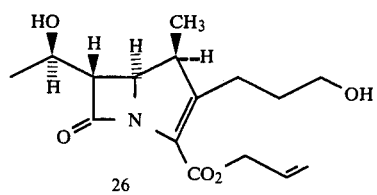

26

Step D

A solution of carbapenem 25 (102 mg, 0.25 mmol), glacial acetic acid (150 mg, 2.5 mmol), and 1M tetrabutyl ammonium fluoride in tetrahydrofuran (1.25 ml, 1.25 mmol) is stirred at ambient temperature for 30 hr. under a nitrogen atmosphere. The reaction mixture is then added to 0.5M pH 7 phosphate buffer (25 ml), water (25 ml), and ethyl acetate (50 ml). The layers are separated and the aqueous layer is extracted with an additional portion of ethyl acetate. The combined organic layers are washed with brine and dried over anhydrous magnesium sulfate. The dried solution is concentrated in vacuo and the residue is chromatographed on silica gel prep plates (eluting with ethyl acetate/hexane) to yield dihydroxycarbapenem 26.

Step B

A solution of the THP ether 23 (772 mg, 1.0 mmol) in 5 ml 80% aqueous tetrahydrofuran is cooled to 0° and treated with 200 μl of trifluoroacetic acid. The mixture is stirred for four hours and then neutralized with solid sodium bicarbonate. The mixture is extracted with ethyl acetate (2×25 ml) and the combined organic layers are washed with brine and dried over anhydrous magnesium sulfate. The dried solution is concentrated in vacuo and the residue is chromatographed on silica gel prep plates (eluting with ethyl acetate/hexane) to yield hydroxyketone 24.

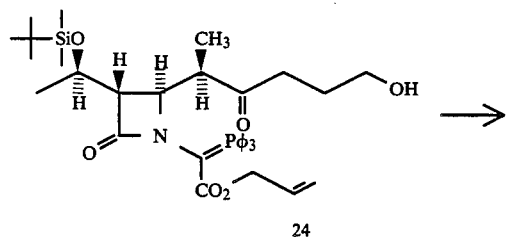

24

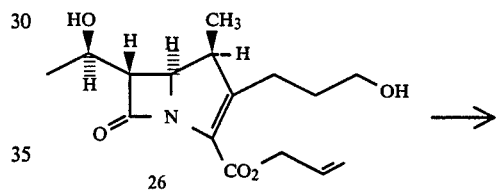

26

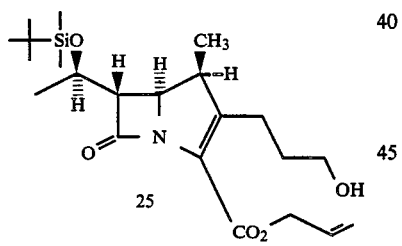

25

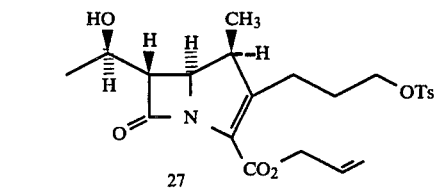

27

Step C

A solution of hydroxyketone 24 (344 mg, 0.50 mmol) in deoxygenated toluene (10 ml) is heated at reflux under an atmosphere of nitrogen for 1.5 hr., then is cooled and concentrated in vacuo. The resulting oil is chromatographed on silica gel prep plates (eluting with ethyl acetate/hexane) to provide hydroxypropyl carbapenem 25.

Step E

A solution of dihydroxycarbapenem 26 (53 mg, 0.18 mmol) and p-toluene sulfonic anhydride (55 mg, 0.18 mmol) in anhydrous methylene chloride (5 ml) is cooled to 0° C. and triethylamine (20 mg, 0.20 mmol) is added slowly by syringe. The resulting solution is stirred at 0° C. for 1 hr, then is diluted with methylene chloride (20 ml) and washed quickly with cold pH 7 phosphate buffer and brine. The organic phase is dried over anhydrous sodium sulfate and the solvent is removed in vacuo to provide crude tosylate 27 which is carried on without further purification.

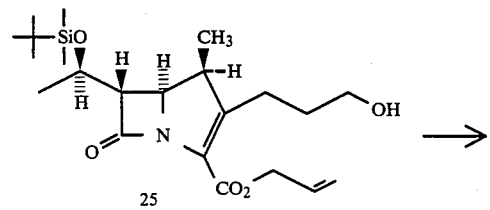

25

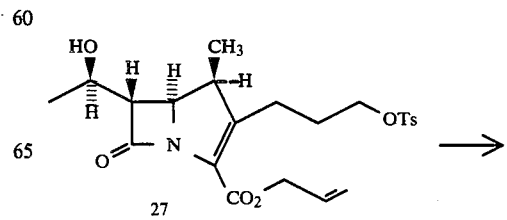

27

-continued

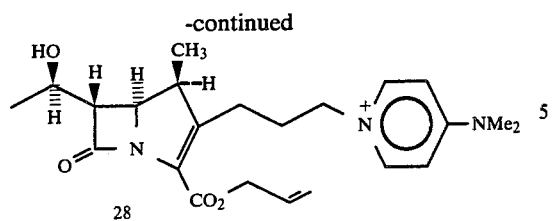
28

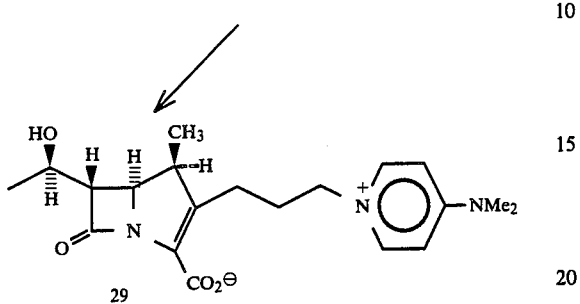
29

Step F

An ice cold solution of crude tosylate 27 (45 mg, 0.10 mmol) in anhydrous actonitrile (5 ml) is treated with 4-dimethylaminopyridine (12.2 mg, 0.10 mmol). The resulting solution is stirred at 0° C. for 10 min., then allowed to warm to room temperature. After four hours the mixture is concentrated in vacuo to give crude pyridinium salt 28. This material is suspended in a mixture of methylene chloride (2 ml) and ethyl acetate (2 ml). To this mixture is added a solution of potassium ethylhexanoate in ethyl acetate (0.360 ml of 0.5M solution, 0.18 mmol), triphenyl phosphine (3.3 mg, 0.013 mmol) and tetrakis(triphenylphosphine)palladium[0](0.5 mg, 0.0005 mmol). The reaction mixture is stirred under nitrogen at ambient temperature for 2 hr., then is concentrated in vacuo. The residue is partitioned between water (5 ml) and ethyl ether (5 ml). The aqueous phase is separated and washed with an additional portion of ether, then is concentrated in vacuo and chromatographed on two RPS plates (eluting with ethanol/water). The U.V. active band is removed from the plates and extracted with 4:1 acetonitrile/water. This solution is washed four times with hexanes, then concentrated in vacuo and lyophilized to yield compound 29.

What is claimed is:

1. A compound having the formula:

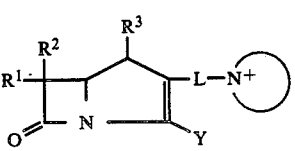
(I.)

wherein:

$R^3$ is hydrogen or methyl;

$R_1$ and $R_2$ are independently H, $CH_3$, $CH_3CH_2—$, $(CH_3)_2CH—$, $HOCH_2$, $CH_3CH(OH)—$, $(CH_3)_2C(OH)—$, $FCH_2—$, $F_2CH$, $F_3C—$, $CH_3CH(F)—$, $CH_3CF_2—$, or $(CH_3)_2 C(F)—$;

wherein

is a quaternary, monocyclic or bicyclic, substituted or unsubstituted heteroaryl group containing (a) when monocyclic, up to 3 heteroatoms and up to 6 total ring atoms or (b) when bicyclic up to 5 heteroatoms and 9-10 ring atoms, which is optionally substituted by one or more of the groups independently selected from (1) a substituted or unsubstituted $C_1-C_6$ alkyl, $C_2-C_6$ alkenyl, $C_5-C_7$ cycloalkenyl, $C_3-C_7$ cycloalkyl, or ($C_3-C_7$ cycloalkyl)methyl;
(2) a substituted or unsubstituted $C_3-C_7$ heterocycloalkyl or ($C_3-C_7$ heterocycloalkyl)methyl having up to 3 hetero ring atoms;
(3) an unsubstituted or substituted phenyl or heteroaryl radical;
(4) an unsubstituted or substituted phenyl ($C_1-C_4$ alkyl) or heteroaryl ($C_1-C_4$ alkyl) radical;
(5) a trifluoromethyl or pentafluoroethyl group;
(6) a halogen atom;
(7) an unsubstituted or substituted $C_1-C_4$ alkoxy radical;
(8) a hydroxyl group;
(9) an unsubstituted or substituted ($C_1-C_6$ alkyl) carbonyloxy radical;
(10) a carbamoyloxy radical which is unsubstituted, monosubstituted or disubstituted on the nitrogen with a $C_1-C_4$ alkyl group;
(11) a $C_1-C_6$ alkylthio radical, $C_1-C_6$ alkylsulfinyl radical or a $C_1-C_6$ alkylsulfonyl radical each of which is unsubstituted or substituted in the alkyl group;
(12) a sulfo group;
(13) a sulfamoyl group which is unsubstituted, monosubstituted, or disubstituted on nitrogen with a $C_1-C_4$ alkyl group;
(14) an amino group;
(15) a mono($C_1-C_4$ alkyl) amino or di($C_1-C_4$ alkyl) amino radical each of which is unsubstituted or substituted in the alkyl group;
(16) a formylamino group;
(17) an unsubstituted or substituted ($C_1-C_6$ alkyl) carbonylamino radical;
(18) a ($C_1-C_4$ alkoxy) carbonylamino radical;
(19) a ureido group in which the terminal nitrogen atom is unsubstituted or monosubstituted with a $C_1-C_6$ alkyl group;
(20) an arylsulfonamido or ($C_1-C_6$ alkyl) sulfonamido group;
(21) a cyano group;
(22) a formyl or acetalized formyl radical;
(23) an unsubstituted or substituted ($C_1-C_6$ alkyl) carbonyl radical wherein the carbonyl group is free or acetalized;
(24) an unsubstituted or substituted phenylcarbonyl or heteroarylcarbonyl radical;
(25) a hydroxyiminomethyl radical in which the oxygen or carbon atom is optionally substituted by a $C_1-C_4$ alkyl group;
(26) a carboxyl group;
(26a) a 5-tetrazolyl group;
(27) a ($C_1-C_6$ alkoxy) carbonyl radical;

(28) a carbamoyl radical which is unsubstituted, monosubstituted, or disubstituted on the nitrogen atom with a $C_1$-$C_4$ alkyl group;

(29) a N-hydroxy carbamoyl or N-($C_1$-$C_4$ alkoxy) carbamoyl radical in which the nitrogen atom may be additionally substituted by a $C_1$-$C_4$ alkyl group;

(30) a thiocarbamoyl group;

(31) an amidino group

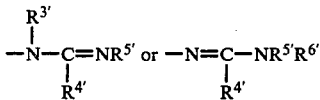

wherein $R^{3'}$, $R^{4'}$, $R^{5'}$, $R^{6'}$ are hydrogen, $C_1$-$C_4$ alkyl, or wherein two of the groups together form a $C_3$-$C_6$ alkylidine radical optionally interupted by a heteroatom and joined to either one or two nitrogen atoms to form a ring;

(32) a guanidino group in which $R^{4'}$ above is $NR^{5'}R^{6'}$;

(33) a carbamimidoyl group

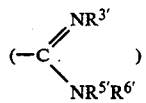

wherein $R^{3'}$, $R^{5'}$ and $R^{6'}$ are as defined above;

(34) a cyano ($C_1$-$C_4$ alkyl) radical;

(35) a carboxy ($C_1$-$C_4$ alkyl) radical;

(36) a sulfo ($C_1$-$C_4$ alkyl) radical;

(37) a carbamoyl ($C_1$-$C_4$ alkyl) radical;

(38) a hydroxy ($C_1$-$C_4$ alkyl) radical;

(39) an amino ($C_1$-$C_6$ alkyl) radical which is unsubstituted, monosubstituted, or disubstituted on the nitrogen atom with $C_1$-$C_4$ alkyl groups; and

(40) a 5-tetrazoyl ($C_1$-$C_4$ alkyl) radical;

wherein the substituents in groups (7), (9), (11), (15), (17), (23), and (24) are selected from hydroxy, $C_1$-$C_4$alkoxy, mercapto, amino, mono- or di($C_1$-$C_4$alkyl)amino, cyano, halo, $CF_3$, COOH, sulfo, carbamoyl, and sulfamoyl, and wherein the substituents in grous (1)–(4) are selected from those defined in groups (5)–(33).

L is a bridging group comprising substituted or unsubstituted $C_1$-$C_4$ straight, $C_2$-$C_6$ branched or $C_3$-$C_7$ cycloalkyl groups wherein the substituents are selected from $C_1$-$C_6$ alkyl, O—$C_1$-$C_6$ alkyl, S—$C_1$-$C_6$ alkyl, $CF_3$, N($C_1$-$C_6$ alkyl)$_2$;

Y is (i) —COOH, a pharmaceutically acceptable ester or salt thereof;

(ii) COOR wherein R is a removeable carboxy protecting group, e.g., p-nitrobenzyl, o-nitrobenzyl, benzyl, or allyl;

(iii) COOM wherein M is an alkali metal; or (iv) COO$^-$ provided that when Y is other than (iv) a counterion $Z^-$ is present.

2. A compound of claim 1 wherein $R^1$ is $CH_3$.

3. A compound of claim 1 wherein L is substituted or unsubstituted branched or linear $C_1$-$C_4$ alkyl.

4. A compound of claim 3 wherein L is —$CH_2$—, —$CH(CH_3)$—, —$(CH_2)_2$—, or —$CH(CH_3)CH_2$—.

5. A compound of claim 1 wherein

is monocyclic heteroarylim having 5-6 ring atoms.

6. A compound of claim 5 wherein

is a pyridinium, diazolium, triazolium, thiazolium or oxazolium group.

7. A compound of claim 1 wherein said heteroarylium ring is substituted by $C_1$-$C_6$ alkyl group, carboxy ($C_1$-$C_4$ alkyl), carbamoyl ($C_1$-$C_4$ alkyl), sulfo ($C_1$-$C_4$ alkyl), heteroaryl ($C_1$-$C_4$ alkyl), or cyano ($C_1$-$C_4$ alkyl).

8. The compound of claim 4 wherein the

group is substituted or unsubstituted pyridinium or pyrazinium, wherein the substituent is $NH_2$, OH, CH=N—$OCH_3$, $C_1$-$C_3$alkyl, $CF_3$, $CONH_2$, COOH, halo, $C_1$-$C_3$alkoxy, $SO_3H$, CHO, CN,

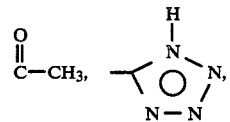

N($C_1$-$C_3$alkyl)$_2$, NH($C_1$-$C_3$alkyl), $CH_2CO_2H$, $CH_2SO_3H$, $CH_2OH$, $CH_2CN$, $CH_2CONH_2$, or $CH_2N(C_1$-$C_3$alkyl)$_2$.

9. The compound of claim 3 wherein L is —$CH_2$—, —$CH_2$—$CH_2$— or

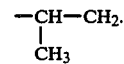

10. The compound of claim 6 wherein

is substituted or unsubstituted pyridinium.

11. The compound of claim 7 wherein said

group is pyridinium, carboxypyridinium, hydroxypyridinium, $C_1$-$C_3$ alkylpyridinium or $diC_1$-$C_3$ alkylaminopyridinium.

12. The compound of claim 8 wherein L is —($CH_2$)$_2$— or —$CH(CH_3)$—$CH_2$—.

13. The compound of claim 9 wherein Y is (iv) and

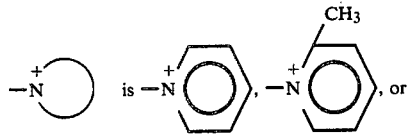

14. The compound of claim 10 wherein

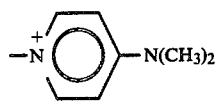

15. The compound of claim 9 wherein

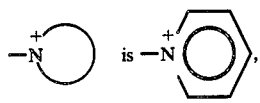

16. The compound of claim 12 wherein

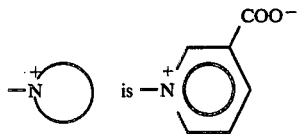

17. A compound of claim 1 having the stereochemical configuration:

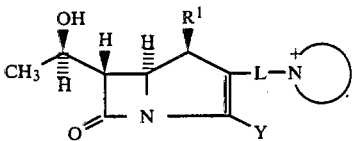

18. A compound of claim 17 wherein $R^1$ is $CH_3$, having a beta configuration.

19. The combination of a compound of claim 1 and a DHP inhibitor.

20. A combination of claim 19 wherein the DHP inhibitor is 7-(L-2-amino-2-carboxyethylthio)-2-(2,2-dimethylcyclopropanecarboxamido)-2-heptenoic acid.

21. A pharmaceutical composition for antibiotic use comprising an antibacterially effective amount of a compound of claim 1, an inhibitorily effective amount of a DHP inhibitor, and, optionally, a pharmaceutically acceptable carrier.

22. A pharmaceutical composition according to claim 14 wherein the DHP inhibitor is 7-(L-2-amino-2-carboxyethylthio)-2-(2,2-dimethylcyclopropanecarboxamido)-2-heptenoic acid.

23. A method of treating bacterial infections in human or animal subjects in need of such treatment comprising coadministering to said subjects an antibacterially effective amount of a compound of claim 1, an inhibitorily effective amount of a DHP inhibitor.

24. A method according to claim 23 wherein the DHP inhibitor is 7-(L-2-amino-2-carboxyethylthio)-2-(2,2-dimethylcyclopropanecarboxamido)-2-heptenoic acid.

25. A pharmaceutical composition for antibiotic use comprising an antibacterially effective amount of a compound of claim 1, and, optionally, a pharmaceutically acceptable carrier.

26. A method of treating bacterial infections in human or animal subjects in need of such treatment comprising administering to said subjects an antibacterially effective amount of a compound of claim 1.

* * * * *